US007014968B2

(12) United States Patent
Tokarski et al.

(10) Patent No.: US 7,014,968 B2
(45) Date of Patent: Mar. 21, 2006

(54) ORGANOPHOTORECEPTOR WITH CHARGE TRANSPORT MATERIAL HAVING A THIIRANYL GROUP

(75) Inventors: Zbigniew Tokarski, Woodbury, MN (US); Nusrallah Jubran, St. Paul, MN (US); Vytautas Getautis, Kaunas (LT); Osvaldas Paliulis, Kaunas (LT); Edmundas Montrimas, Vilnius (LT); Valentas Gaidelis, Vilnius (LT)

(73) Assignee: Samsung Electronics Co., Ltd., Suwon (KR)

( * ) Notice: Subject to any disclaimer, the term of this patent is extended or adjusted under 35 U.S.C. 154(b) by 248 days.

(21) Appl. No.: 10/749,178

(22) Filed: Dec. 30, 2003

(65) Prior Publication Data

US 2005/0147904 A1    Jul. 7, 2005

(51) Int. Cl.
G03G 5/00    (2006.01)
G03G 15/06    (2006.01)
C07D 327/02    (2006.01)

(52) U.S. Cl. .............................. 430/75; 430/77; 430/79; 430/58.05; 430/126; 399/159; 549/1; 549/90

(58) Field of Classification Search .................. 430/75, 430/77, 79, 58.05, 126; 399/159; 549/1, 549/90
See application file for complete search history.

(56) References Cited

U.S. PATENT DOCUMENTS

| 4,297,426 A | 10/1981 | Sakai et al. |
| 4,786,571 A | 11/1988 | Ueda |
| 4,971,870 A | 11/1990 | Kato et al. |
| 4,971,871 A | 11/1990 | Kato et al. |
| 4,977,049 A | 12/1990 | Kato et al. |
| 5,294,507 A | 3/1994 | Kato et al. |
| 5,368,931 A | 11/1994 | Kato et al. |
| 5,455,135 A | 10/1995 | Maruyama et al. |
| 5,800,602 A | 9/1998 | Baur et al. |
| 5,942,615 A | 8/1999 | Kobayashi et al. |
| 6,066,426 A | 5/2000 | Mott et al. |
| 6,083,651 A | 7/2000 | Kobayashi et al. |
| 6,140,004 A | 10/2000 | Mott et al. |
| 6,340,548 B1 | 1/2002 | Jubran et al. |
| 6,451,505 B1 | 9/2002 | Patel et al. |
| 6,214,503 B1 | 4/2003 | Gaidelis et al. |

FOREIGN PATENT DOCUMENTS

| DE | 816923 | 12/1959 |
| EP | 1465020 | 10/2004 |
| JP | 2001-166519 | 5/1987 |

OTHER PUBLICATIONS

P.M. Thangamathesvaran and S.R. Jain, "Synthesis, Characterization and Binding Properties of Epoxy Resins Based On Carbonohydrazones And Thiocarbonohydrazones," Frontiers of Polymer Research, p. 589-594, Edited by P.N. Prasad and J.K. Nigam, Plenum Press, NY, 1991.
S.R.Jain et el, "Novel Energetic N-N Bonded Polymeric Binders for Composite Propellants," Macromolecules New Frontiers, p. 1018-1021, Allied Publishers Ltd., New Delhi, 1998.
M. Daskeviciene et el., "Derivatives of 2,5-Dimercapto-1,3,4-thiazole as Hole Transporting Materials," Lithuanian Journal of Physics, 2001, 41, No. 4-6, 521-526.
Chemical Abstracts Columbus, Ohio, vol. 91, No. 14, 1979, Abstract No. 115374w, p. 516, Column 2, XP-002324620.
Chemical Abstracts Columbus, Ohio, vol. 98, No. 22, 1983, Abstract No. 189050d, p. 600, Column 1, XP-002324619.
Chemical Abstracts Columbus, Ohio, vol. 77, No. 25, 1972, Abstract No. 16433d, p. 384, XP-002324618.
Andruleviciute et al., "Cationic photopolymerization of carbazolyl- and phenothiazinyl-containing thirranes", *Journal of Photochemistry and Photobiology A: Chemistry*, 147:63-63 (2002).

Primary Examiner—Mark A. Chapman
(74) *Attorney, Agent, or Firm*—Patterson, Thuente, Skaar & Christensen, P.A.

(57) ABSTRACT

Improved organophotoreceptor comprises a photoconductive element comprising:
(a) a charge transport material having the formula

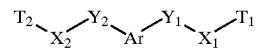

where $Y_1$ and $Y_2$ are, each independently, a bond, $-CR_1=N-NR_2-$, or $-CR_3=N-N=CR_4-$ where $R_1$, $R_2$, $R_3$, and $R_4$ comprise, each independently, H, an alkyl group, an alkenyl group, a heterocyclic group, or an aromatic group;
$X_1$ and $X_2$ are, each independently, a linking group;
$T_1$ and $T_2$ are, each independently, a thiiranyl group, H, an alkyl group, an alkenyl group, or an aromatic group with the proviso that at least one of $T_1$ and $T_2$ is a thiiranyl group; and
Ar comprises an aromatic group with the proviso that when both $Y_1$ and $Y_2$ are a bond and one of $T_1$ and $T_2$ is not a thiiranyl group, Ar comprises a bis[(N,N-disubstituted)amino]aromatic group or a bicarbazole group; and
(b) a charge generating compound.

Corresponding electrophotographic apparatuses and imaging methods are described.

76 Claims, No Drawings

ORGANOPHOTORECEPTOR WITH CHARGE TRANSPORT MATERIAL HAVING A THIIRANYL GROUP

FIELD OF THE INVENTION

This invention relates to organophotoreceptors suitable for use in electrophotography and, more specifically, to organophotoreceptors having a charge transport material comprising at least a thiiranyl group. The thiiranyl group(s) may or may not be covalently bonded with a polymeric binder, directly or through a crosslinking compound.

BACKGROUND OF THE INVENTION

In electrophotography, an organophotoreceptor in the form of a plate, disk, sheet, belt, drum or the like having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas where light strikes the surface, thereby forming a pattern of charged and uncharged areas, referred to as a latent image. A liquid or dry toner is then provided in the vicinity of the latent image, and toner droplets or particles deposit in the vicinity of either the charged or uncharged areas to create a toned image on the surface of the photoconductive layer. The resulting toned image can be transferred to a suitable ultimate or intermediate receiving surface, such as paper, or the photoconductive layer can operate as an ultimate receptor for the image. The imaging process can be repeated many times to complete a single image, for example, by overlaying images of distinct color components or effect shadow images, such as overlaying images of distinct colors to form a full color final image, and/or to reproduce additional images.

Both single layer and multilayer photoconductive elements have been used. In single layer embodiments, a charge transport material and charge generating material are combined with a polymeric binder and then deposited on the electrically conductive substrate. In multilayer embodiments, the charge transport material and charge generating material are present in the element in separate layers, each of which can optionally be combined with a polymeric binder, deposited on the electrically conductive substrate. Two arrangements are possible for a two-layer photoconductive element. In one two-layer arrangement (the "dual layer" arrangement), the charge-generating layer is deposited on the electrically conductive substrate and the charge transport layer is deposited on top of the charge generating layer. In an alternate two-layer arrangement (the "inverted dual layer" arrangement), the order of the charge transport layer and charge generating layer is reversed.

In both the single and multilayer photoconductive elements, the purpose of the charge generating material is to generate charge carriers (i.e., holes and/or electrons) upon exposure to light. The purpose of the charge transport material is to accept at least one type of these charge carriers and transport them through the charge transport layer in order to facilitate discharge of a-surface charge on the photoconductive element. The charge transport material can be a charge transport compound, an electron transport compound, or a combination of both. When a charge transport compound is used, the charge transport compound accepts the hole carriers and transports them through the layer with the charge transport compound. When an electron transport compound is used, the electron transport compound accepts the electron carriers and transports them through the layer with the electron transport compound.

Organophotdreceptors may be used for both dry and liquid electrophotography. There are many differences between dry and liquid electrophotography. The most obvious difference is that a dry toner is used in dry electrophotography, whereas a liquid toner is used in liquid electrophotography. A potential advantage of liquid electrophotography is that it can provide an improved resolution and thus sharper images than dry electrophotography because liquid toner particles can generally be significantly smaller than dry toner particles. As a result of their smaller size, liquid toners are able to provide images of higher optical density per toner mass.

In both dry and liquid electrophotography, the charge transport material used for the organophotoreceptor is required to be compatible with the polymeric binder in the photoconductive element. The requirement puts an undesirable limitation in choosing a suitable polymeric binder for a particular charge transport material. If the charge transport material is not compatible with the polymeric binder, the charge transport material may phase-separate or crystallize in the polymeric binder matrix, or may diffuse onto the surface of the layer containing the charge transport material. If such incompatibility occurs, the organophotoreceptor may cease to transport charge.

Furthermore, liquid electrophotography faces an additional problem. The problem is that the organophotoreceptor for liquid electrophotography is in frequent contact with the liquid carrier of a liquid toner. As a result, the charge transport material in the photoconductive element may be removed by constant extraction by the liquid carrier. Over a long period of operation, the amount of the charge transport material removed by extraction may be significant, and such removal may be detrimental to the performance of the organophotoreceptor.

SUMMARY OF THE INVENTION

This invention provides organophotoreceptors having good electrostatic properties such as high $V_{acc}$ and low $V_{dis}$. This invention also provides charge transport materials having a high compatibility with the polymeric binder, minimal phase separation, and minimal extraction by liquid carriers.

In a first aspect, an organophotoreceptor comprises an electrically conductive substrate and a photoconductive element on the electrically conductive substrate, the photoconductive element comprising:

(a) a charge transport material having the formula

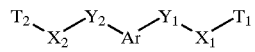

where $Y_1$ and $Y_2$ are, each independently, a bond, $-CR_1=N-NR_2-$, or $-CR_3=N-N=CR_4-$ where $R_1$, $R_2$, $R_3$, and $R_4$ comprise, each independently, H, an alkyl group, an alkenyl group, a heterocyclic group, or an aromatic group;

$X_1$ and $X_2$ are, each independently, a linking group having the formula $-(CH_2)_m-$, branched or linear, where m is an integer between 0 and 20, inclusive, and one or more of the methylene groups is optionally replaced by O, S, C=O, O=S=O, a heterocyclic group, an aromatic group, urethane, urea, an ester group, an $NR_5$ group, a $CHR_6$ group, or a $CR_7R_8$ group where $R_5$, $R_6$, $R_7$, and $R_8$ comprise, each independently, H, hydroxyl group, thiol group, an alkyl group, an alkenyl group, a heterocyclic group, or an aromatic group;

$T_1$ and $T_2$ are, each independently, a thiiranyl group, H, an alkyl group, an alkenyl group, or an aromatic group with the proviso that at least one of $T_1$ and $T_2$ is a thiiranyl group; and Ar comprises an aromatic group with the proviso that when both $Y_1$ and $Y_2$ are a bond and one of $T_1$ and $T_2$ is not a thiiranyl group, Ar comprises a bis[(N,N-disubstituted)amino]aromatic group or a bicarbazole group; and (b) a charge generating compound.

The organophotoreceptor may be provided, for example, in the form of a plate, a flexible belt, a flexible disk, a sheet, a rigid drum, or a sheet around a rigid or compliant drum. In one embodiment, the organophotoreceptor includes: (a) a photoconductive element comprising the charge transport material, the charge generating compound, a second charge transport material, and a polymeric binder; and (b) the electrically conductive substrate.

In a second aspect, the invention features an electrophotographic imaging apparatus that comprises (a) a light imaging component; and (b) the above-described organophotoreceptor oriented to receive light from the light imaging component. The apparatus can further comprise a liquid toner dispenser. The method of electrophotographic imaging with photoreceptors containing the above noted charge transport materials is also described.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of at least relatively charged and uncharged areas on the surface; (c) contacting the surface with a toner, such as a liquid toner that includes a dispersion of colorant particles in an organic liquid, to create a toned image; and (d) transferring the toned image to a substrate.

In a fourth aspect, the invention features a charge transport material having the general formula above.

In a fifth aspect, the invention features a polymeric charge transport compound prepared by the reaction of a functional group in a polymeric binder with at least a thiiranyl group in a compound having the formula

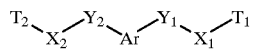

where $Y_1$ and $Y_2$ are, each independently, a bond, —$CR_1$=N—$NR_2$—, or —$CR_3$=N—N=$CR_4$— where $R_1$, $R_2$, $R_3$, and $R_4$ comprise, each independently, H, an alkyl group, an alkenyl group, a heterocyclic group, or an aromatic group;

$X_1$ and $X_2$ are, each independently, a linking group having the formula —$(CH_2)_m$—, branched or linear, where m is an integer between 0 and 20, inclusive, and one or more of the methylene groups is optionally replaced by O, S, C=O, O=S=O, a heterocyclic group, an aromatic group, urethane, urea, an ester group, an $NR_5$ group, a $CHR_6$ group, or a $CR_7R_8$ group where $R_5$, $R_6$, $R_7$, and $R_8$ comprise, each independently, H, hydroxyl group, thiol group, an alkyl group, an alkenyl group, a heterocyclic group, or an aromatic group;

$T_1$ and $T_2$ are, each independently, a thiiranyl group, H, an alkyl group, an alkenyl group, or an aromatic group with the proviso that at least one of $T_1$ and $T_2$ is a thiiranyl group; and Ar comprises an aromatic group with the proviso that when both $Y_1$ and $Y_2$ are a bond and one of $T_1$ and $T_2$ is not a thiiranyl group, Ar comprises a bis[(N,N-disubstituted)amino]aromatic group or a bicarbazole group.

In sixth aspect, the invention features an organophotoreceptor comprising an electrically conductive substrate and a photoconductive element on the electrically conductive substrate, the photoconductive element comprising:

(a) the polymeric charge transport compound described above; and (b) a charge generating compound.

The invention provides suitable charge transport materials for organophotoreceptors featuring a combination of good mechanical and electrostatic properties. These photoreceptors can be used successfully with liquid toners to produce high quality images. The high quality of the imaging system can be maintained after repeated cycling.

Other features and advantages of the invention will be apparent from the following description of the particular embodiments thereof, and from the claims.

DETAILED DESCRIPTION OF PREFERRED EMBODIMENTS

An organophotoreceptor as described herein has an electrically conductive substrate and a photoconductive element comprising a charge generating compound and a charge transport material having at least a thiiranyl group attached through a linking group to either a hydrazone, a diazine, or an aromatic group. These charge transport materials have desirable properties as evidenced by their performance in organophotoreceptors for electrophotography. In particular, the charge transport materials of this invention have high charge carrier mobilities and good compatibility with various binder materials, and possess excellent electrophotographic properties. The organophotoreceptors according to this invention generally have a high photosensitivity, a low residual potential, and a high stability with respect to cycle testing, crystallization, and organophotoreceptor bending and stretching. The organophotoreceptors are particularly useful in laser printers and the like as well as fax machines, photocopiers, scanners and other electronic devices based on electrophotography. The use of these charge transport materials is described in more detail below in the context of laser printer use, although their application in other devices operating by electrophotography can be generalized from the discussion below.

To produce high quality images, particularly after multiple cycles, it is desirable for the charge transport materials to form a homogeneous solution with the polymeric binder and remain approximately homogeneously distributed through the organophotoreceptor material during the cycling of the material. In addition, it is desirable to increase the amount of charge that the charge transport material can accept (indicated by a parameter known as the acceptance voltage or "$V_{acc}$"), and to reduce retention of that charge upon discharge (indicated by a parameter known as the discharge voltage or "$V_{dis}$").

The charge transport materials can be classified as a charge transport compound or an electron transport compound. There are many charge transport compounds and electron transport compounds known in the art for electrophotography. Non-limiting examples of charge transport compounds include, for example, pyrazoline derivatives, fluorene derivatives, oxadiazole derivatives, stilbene derivatives, enamine derivatives, enamine stilbene derivatives, hydrazone derivatives, carbazole hydrazone derivatives, (N,N-disubstituted)arylamines such as triaryl amines, polyvinyl carbazole, polyvinyl pyrene, polyacenaphthylene, or multi-hydrazone compounds comprising at least two hydrazone groups and at least two groups selected from the group consisting of (N,N-disubstituted)arylamine such as triphenylamine and heterocycles such as carbazole, julolidine, phenothiazine, phenazine, phenoxazine, phenoxathiin, thiazole, oxazole, isoxazole, dibenzo(1,4)dioxin, thianthrene, imidazole, benzothiazole, benzotriazole, benzoxazole, benzimidazole, quinoline, isoquinoline, quinoxaline, indole, indazole, pyrrole, purine, pyridine, pyridazine, pyrimidine, pyrazine, triazole, oxadiazole, tetrazole, thiadiazole, benzisoxazole, benzisothiazole, dibenzofuran, dibenzothiophene, thiophene, thianaphthene, quinazoline, or cinnoline.

Non-limiting examples of electron transport compounds include, for example, bromoaniline, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-indeno[1,2-b]thiophene-4-one, and 1,3,7-trinitrodibenzo thiophene-5,5-dioxide, (2,3-diphenyl-1-indenylidene)malononitrile, 4H-thiopyran-1,1-dioxide and its derivatives such as 4-dicyanomethylene-2,6-diphenyl-4H-thiopyran-1,1-dioxide, 4-dicyanomethylene-2,6-di-m-tolyl-4H-thiopyran-1,1-dioxide, and unsymmetrically substituted 2,6-diaryl-4H-thiopyran-1,1-dioxide such as 4H-1,1-dioxo-2-(p-isopropylphenyl)-6-phenyl-4-(dicyanomethylidene)thiopyran and 4H-1,1-dioxo-2-(p-isopropylphenyl)-6-(2-thienyl)-4-(dicyanomethylidene) thiopyran, derivatives of phospha-2,5-cyclohexadiene, alkoxycarbonyl-9-fluorenylidene)malononitrile derivatives such as (4-n-butoxycarbonyl-9-fluorenylidene)malononitrile, (4-phenethoxycarbonyl-9-fluorenylidene)malononitrile, (4-carbitoxy-9-fluorenylidene)malononitrile, and diethyl(4-n-butoxycarbonyl-2,7-dinitro-9-fluorenylidene)-malonate, anthraquinodimethane derivatives such as 11,11,12,12-tetracyano-2-alkylanthraquinodimethane and 11,11-dicyano-12,12-bis(ethoxycarbonyl)anthraquinodimethane, anthrone derivatives such as 1-chloro-10-[bis(ethoxycarbonyl)methylene]anthrone, 1,8-dichloro-10-[bis(ethoxycarbonyl)methylene]anthrone, 1,8-dihydroxy-10-[bis(ethoxycarbonyl)methylene]anthrone, and 1-cyano-10-[bis(ethoxycarbonyl)methylene]anthrone, 7-nitro-2-aza-9-fluoroenylidene-malononitrile, diphenoquinone derivatives, benzoquinone derivatives, naphtoquinone derivatives, quinine derivatives, tetracyanoethylenecyanoethylene, 2,4,8-trinitro thioxantone, dinitrobenzene derivatives, dinitroanthracene derivatives, dinitroacridine derivatives, nitroanthraquinone derivatives, dinitroanthraquinone derivatives, succinic anhydride, maleic anhydride, dibromo maleic anhydride, pyrene derivatives, carbazole derivatives, hydrazone derivatives, N,N-dialkylaniline derivatives, diphenylamine derivatives, triphenylamine derivatives, triphenylmethane derivatives, tetracyano quinoedimethane, 2,4,5,7-tetranitro-9-fluorenone, 2,4,7-trinitro-9-dicyanomethylene fluorenone, 2,4,5,7-tetranitroxanthone derivatives, and 2,4,8-trinitrothioxanthone derivatives. In some embodiments of interest, the electron transport compound comprises an (alkoxycarbonyl-9-fluorenylidene)malononitrile derivative, such as (4-n-butoxycarbonyl-9-fluorenylidene) malononitrile.

Although there are many charge transport materials available, there is a need for other charge transport materials to meet the various requirements of particular electrophotography applications.

In electrophotography applications, a charge-generating compound within an organophotoreceptor absorbs light to form electron-hole pairs. These electrons and holes can be transported over an appropriate time frame under a large electric field to discharge locally a surface charge that is generating the field. The discharge of the field at a particular location results in a surface charge pattern that essentially matches the pattern drawn with the light. This charge pattern then can be used to guide toner deposition. The charge transport materials described herein are especially effective at transporting charge, and in particular holes from the electron-hole pairs formed by the charge generating compound. In some embodiments, a specific electron transport compound or charge transport compound can also be used along with the charge transport material of this invention.

The layer or layers of materials containing the charge generating compound and the charge transport materials are within an organophotoreceptor. To print a two dimensional image using the organophotoreceptor, the organophotoreceptor has a two dimensional surface for forming at least a portion of the image. The imaging process then continues by cycling the organophotoreceptor to complete the formation of the entire image and/or for the processing of subsequent images.

The organophotoreceptor may be provided in the form of a plate, a flexible belt, a disk, a rigid drum, a sheet around a rigid or compliant drum, or the like. The charge transport material can be in the same layer as the charge generating compound and/or in a different layer from the charge generating compound. Additional layers can be used also, as described further below.

In some embodiments, the organophotoreceptor material comprises, for example: (a) a charge transport layer comprising the charge transport material and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate. In further embodiments, the organophotoreceptor material has a single layer with both a charge transport material and a charge generating compound within a polymeric binder.

The organophotoreceptors can be incorporated into an electrophotographic imaging apparatus, such as laser printers. In these devices, an image is formed from physical embodiments and converted to a light image that is scanned onto the organophotoreceptor to form a surface latent image. The surface latent image can be used to attract toner onto the surface of the organophotoreceptor, in which the toner image is the same or the negative of the light image projected onto the organophotoreceptor. The toner can be a liquid toner or a dry toner. The toner is subsequently transferred, from the surface of the organophotoreceptor, to a receiving surface, such as a sheet of paper. After the transfer of the toner, the entire surface is discharged, and the material is ready to cycle again. The imaging apparatus can further comprise, for example, a plurality of support rollers for transporting a paper receiving medium and/or for movement of the photoreceptor, a light imaging component with suitable optics to form the light image, a light source, such as a laser, a toner source and delivery system and an appropriate control system.

An electrophotographic imaging process generally can comprise (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) exposing the surface with a toner, such as a liquid toner that includes a dispersion of colorant particles in an organic liquid to create a toner image, to attract toner to the charged or discharged regions of the organophotoreceptor; and (d) transferring the toner image to a substrate.

As described herein, an organophotoreceptor comprises a charge transport material having the formula

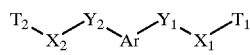

where $Y_1$ and $Y_2$ are, each independently, a bond, $-CR_1=N-NR_2-$, or $-CR_3=N-N=CR_4-$ where $R_1$, $R_2$, $R_3$, and $R_4$ comprise, each independently, H, an alkyl group, an alkenyl group, a heterocyclic group, or an aromatic group;

$X_1$ and $X_2$ are, each independently, a linking group having the formula $-(CH_2)_m-$, branched or linear, where m is an integer between 0 and 20, inclusive, and one or more of the methylene groups is optionally replaced by O, S, C=O, O=S=O, a heterocyclic group, an aromatic group, urethane, urea, an ester group, an $NR_5$ group, a $CHR_6$ group, or a $CR_7R_8$ group where $R_5$, $R_6$, $R_7$, and $R_8$ comprise, each independently, H, hydroxyl group, thiol group, an alkyl group, an alkenyl group, a heterocyclic group, or an aromatic group;

$T_1$ and $T_2$ are, each independently, a thiiranyl group, H, an alkyl group, an alkenyl group, or an aromatic group with the proviso that at least one of $T_1$ and $T_2$ is a thiiranyl group; and Ar comprises an aromatic group with the proviso that when both $Y_1$ and $Y_2$ are a bond and one of $T_1$ and $T_2$ is not a thiiranyl group, Ar comprises a bis[(N,N-disubstituted) amino]aromatic group or a bicarbazolyl group.

An aromatic group can be any conjugated system containing 4n+2π-electrons. There are many criteria available for determining aromaticity. A widely employed criterion for the quantitative assessment of aromaticity is the resonance energy. In general, the resonance energy of the aromatic group is greater than 10 KJ/mol. Aromatic groups may be classified as an aromatic heterocylic group which contains at least a heteroatom in the 4n+2π-electron ring, or as an aryl group which does not contain a heteroatom in the 4n+2π-electron ring. Nonetheless, either the aromatic heterocylic or the aryl group may have at least one heteroatom in a substitutent attached to the 4n+2π-electron ring. Furthermore, either the aromatic heterocylic or the aryl group may comprise a monocyclic or polycyclic (such as bicyclic, tricyclic, etc.) aromatic ring.

Non-limiting examples of the aromatic heterocylic group are furanyl, thiophenyl, pyrrolyl, indolyl, carbazolyl, benzofuranyl, benzothiophenyl, dibenzofuranyl, dibenzothiophenyl, pyridinyl, pyridazinyl, pyrimidinyl, pyrazinyl, triazinyl, tetrazinyl, petazinyl, quinolinyl, isoquinolinyl, cinnolinyl, phthalazinyl, quinazolinyl, quinoxalinyl, naphthyridinyl, pteridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4)dioxinyl, thianthrenyl, and a combination thereof. The aromatic heterocyclic group may also include any combination of the above aromatic heterocyclic groups bonded together either by a bond (as in bicarbazolyl) or by a linking group (as in 1,6di(10H-10-phenothiazinyl)hexane). The linking group may include an aliphatic group, an aromatic group, a heterocyclic group, or a combination thereof. Furthermore, either an aliphatic group or an aromatic group within a linking group may comprise at least one heteroatom such as O, S, and N. Non-limiting examples of the aryl group are phenyl, naphthyl, benzyl, or tolanyl group, sexiphenylene, phenanthrenyl, anthracenyl, coronenyl, and tolanylphenyl. The aryl group may also include any combination of the above aryl groups bonded together either by a bond (as in biphenyl group) or a linking group (as in stilbenyl, diphenyl sulfone, an arylamine group). The linking group may include an aliphatic group, an aromatic group, a heterocyclic group, or a combination thereof. Furthermore, either an aliphatic group or an aromatic group within a linking group may comprise at least one heteroatom such as O, S, and N.

An arylamine group includes p-(N,N-disubstituted)arylamine group (e.g., triphenylamine, diethylphenylamine, and ethyldiphenylamine group), carbazolyl group, and julolidinyl group. A bis[(N,N-disubstituted)amino]aromatic group contains a monocyclic, bicyclic, or polycyclic aromatic ring and two (N,N-disubstituted)amino groups directly linked to the monocyclic or polycyclic (such as bicyclic, tricyclic, etc.) aromatic ring. Non-limiting examples of the bis[(N,N-disubstituted)amino]aromatic group are 1,3-bis(4,4'-dimethyl-diphenylamino)phenyl and 1,3-bis(diphenylamino)phenyl.

Substitution is liberally allowed on the chemical groups to affect various physical effects on the properties of the compounds, such as mobility, sensitivity, solubility, stability, and the like, as is known generally in the art. In the description of chemical substituents, there are certain practices common to the art that are reflected in the use of language. The term group indicates that the generically recited chemical entity (e.g., alkyl group, alkenyl group, aromatic group, thiiranyl group, etc.) may have any substituent thereon which is consistent with the bond structure of that group. For example, where the term 'alkyl group' is used, that term would not only include unsubstituted linear, branched and cyclic alkyls, such as methyl, ethyl, isopropyl, tert-butyl, cyclohexyl, dodecyl and the like, but also substituents having heteroatom such as 3-ethoxylpropyl, 4-(N-ethylamino)butyl, 3-hydroxypentyl, 2-thiolhexyl, 1,2,3-tribromoopropyl, and the like. However, as is consistent with such nomenclature, no substitution would be included within the term that would alter the fundamental bond structure of the underlying group. For example, where a phenyl group is recited, substitution such as 1-aminophenyl, 2,4-dihydroxyphenyl, 1,3,5-trithiophenyl, 1,3,5-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form because of the substitution. When referring to a thiiranyl group, the substituent cited will include any substitution that does not destroy the 3-membered ring structure of the thiiranyl group. Where the term moiety is used, such as alkyl moiety or phenyl moiety, that terminology indicates that the chemical moiety is not substituted. When referring to an alkyl moiety, the term represents only an unsubstituted alkyl hydrocarbon group, whether branched, straight chain, or cyclic.

Organophotoreceptors

The organophotoreceptor may be, for example, in the form of a plate, a sheet, a flexible belt, a disk, a rigid drum, or a sheet around a rigid or compliant drum, with flexible belts and rigid drums generally being used in commercial embodiments. The organophotoreceptor may comprise, for example, an electrically conductive substrate and on the electrically conductive substrate a photoconductive element in the form of one or more layers. The photoconductive element can comprise both a charge transport material and a charge generating compound in a polymeric binder, which may or may not be in the same layer, as well as a second charge transport material such as a charge transport compound or an electron transport compound in some embodiments. For example, the charge transport material and the charge generating compound can be in a single layer. In other embodiments, however, the photoconductive element comprises a bilayer construction featuring a charge generating layer and a separate charge transport layer. The charge generating layer may be located intermediate between the electrically conductive substrate and the charge transport layer. Alternatively, the photoconductive element may have a structure in which the charge transport layer is intermediate between the electrically conductive substrate and the charge generating layer.

The electrically conductive substrate may be flexible, for example in the form of a flexible web or a belt, or inflexible, for example in the form of a drum. A drum can have a hollow cylindrical structure that provides for attachment of the drum to a drive that rotates the drum during the imaging process. Typically, a flexible electrically conductive substrate comprises an electrically insulating substrate and a thin layer of electrically conductive material onto which the photoconductive material is applied.

The electrically insulating substrate may be paper or a film forming polymer such as polyester (e.g., polyethylene terephthalate or polyethylene naphthalate), polyimide, polysulfone, polypropylene, nylon, polyester, polycarbonate, polyvinyl resin, polyvinyl fluoride, polystyrene and the like. Specific examples of polymers for supporting substrates included, for example, polyethersulfone (Stabar™ S-100, available from ICI), polyvinyl fluoride (Tedlar®, available from E.I. DuPont de Nemours & Company), polybisphenol-A polycarbonate (Makrofol™, available from Mobay Chemical Company) and amorphous polyethylene terephthalate (Melinar™, available from ICI Americas, Inc.). The electrically conductive materials may be graphite, dispersed carbon black, iodine, conductive polymers such as polypyrroles and Calgon® conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. In embodiments of particular interest, the electrically conductive material is aluminum. Generally, the photoconductor substrate has a thickness adequate to provide the required mechanical stability. For example, flexible web substrates generally have a thickness from about 0.01 to about 1 mm, while drum substrates generally have a thickness from about 0.5 mm to about 2 mm.

The charge generating compound is a material that is capable of absorbing light to generate charge carriers, such as a dye or pigment. Non-limiting examples of suitable charge generating compounds include, for example, metal-free phthalocyanines (e.g., ELA 8034 metal-free phthalocyanine available from H.W. Sands, Inc. or Sanyo Color Works, Ltd., CGM-X01), metal phthalocyanines such as titanium phthalocyanine, copper phthalocyanine, oxytitanium phthalocyanine (also referred to as titanyl oxyphthalocyanine, and including any crystalline phase or mixtures of crystalline phases that can act as a charge generating compound), hydroxygallium phthalocyanine, squarylium dyes and pigments, hydroxy-substituted squarylium pigments, perylimides, polynuclear quinones available from Allied Chemical Corporation under the trade name Indofast® Double Scarlet, Indofast® Violet Lake B, Indofast® Brilliant Scarlet and Indofast® Orange, quinacridones available from DuPont under the trade name Monastral™ Red, Monastral™ Violet and Monastral™ Red Y, naphthalene 1,4,5,8-tetracarboxylic acid derived pigments including the perinones, tetrabenzoporphyrins and tetranaphthaloporphyrins, indigo- and thioindigo dyes, benzothioxanthene-derivatives, perylene 3,4,9,10-tetracarboxylic acid derived pigments, polyazo-pigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulphoselenide, cadmium selenide, cadmium sulphide, and mixtures thereof For some embodiments, the charge generating compound comprises oxytitanium phthalocyanine (e.g., any phase thereof), hydroxygallium phthalocyanine or a combination thereof.

The photoconductive layer of this invention may optionally contain a second charge transport material which may be a charge transport compound, an electron transport compound, or a combination of both. Generally, any charge transport compound or electron transport compound known in the art can be used as the second charge transport material.

An electron transport compound and a UV light stabilizer can have a synergistic relationship for providing desired electron flow within the photoconductor. The presence of the UV light stabilizers alters the electron transport properties of the electron transport compounds to improve the electron transporting properties of the composite. UV light stabilizers can be ultraviolet light absorbers or ultraviolet light inhibitors that trap free radicals.

UV light absorbers can absorb ultraviolet radiation and dissipate it as heat. UV light inhibitors are thought to trap free radicals generated by the ultraviolet light and after trapping of the free radicals, subsequently to regenerate active stabilizer moieties with energy dissipation. In view of the synergistic relationship of the UV stabilizers with electron transport compounds, the particular advantages of the UV stabilizers may not be their UV stabilizing abilities, although the UV stabilizing ability may be further advantageous in reducing degradation of the organophotoreceptor over time. The improved synergistic performance of organophotoreceptors with layers comprising both an electron transport compound and a UV stabilizer are described further in copending U.S. patent application Ser. No. 10/425, 333 filed on Apr. 28, 2003 to Zhu, entitled "Organophotoreceptor With A Light Stabilizer," incorporated herein by reference.

Non-limiting examples of suitable light stabilizer include, for example, hindered trialkylamines such as Tinuvin 144 and Tinuvin 292 (from Ciba Specialty Chemicals, Terrytown, N.Y.), hindered alkoxydialkylamines such as Tinuvin 123 (from Ciba Specialty Chemicals), benzotriazoles such as Tinuvan 328, Tinuvin 900 and Tinuvin 928 (from Ciba Specialty Chemicals), benzophenones such as Sanduvor 3041 (from Clariant Corp., Charlotte, N.C.), nickel compounds such as Arbestab (from Robinson Brothers Ltd, West Midlands, Great Britain), salicylates, cyanocinnamates, benzylidene malonates, benzoates, oxanilides such as Sanduvor VSU (from Clariant Corp., Charlotte, N.C.), triazines such as Cyagard UV-1164 (from Cytec Industries Inc., N.J.), polymeric sterically hindered amines such as Luchem (from Atochem North America, Buffalo, N.Y.). In some embodiments, the light stabilizer is selected from the group consisting of hindered trialkylamines having the following formula:

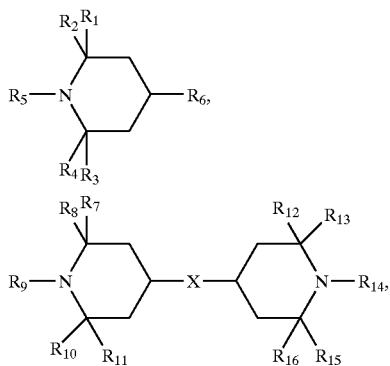

where $R_1$, $R_2$, $R_3$, $R_4$, $R_6$, $R_7$, $R_8$, $R_{10}$, $R_{11}$, $R_{12}$, $R_{13}$, $R_{14}$, $R_{15}$ are, each independently, hydrogen, alkyl group, or ester, or ether group; and $R_5$, $R_9$, and $R_{14}$ are, each independently, alkyl group; and X is a linking group selected from the group consisting of —O—CO—$(CH_2)_m$—CO—O— where m is between 2 to 20.

Optionally, the photoconductive layer may comprise a crosslinking agent linking the charge transport compound and the binder. As is generally true for crosslinking agents in various contexts, the crosslinking agent comprises a plurality of functional groups or at least one functional group with the ability to exhibit multiple functionality. Specifically, a suitable crosslinking agent generally comprises at least one functional group that reacts with a thiiranyl group and at least one functional group reactive with a functional group of the polymeric binder. Suitable functional groups for reacting with the thiiranyl group include, for example, a reactive functionality, such as hydroxyl, thiol, an amino group, a carboxyl group, or a combination thereof. In some embodiments, the functional group for reacting with the polymeric binder does not react significantly with the thiiranyl group. In general, a person of ordinary skill in the art can select the appropriate functional group of the crosslinking agent to react with the polymeric binder, or similarly, a person of ordinary skill in the art can select appropriate functional groups of the polymeric binder to react with the functional group of the crosslinking agent. Suitable functional groups of the crosslinking agent that do not react significantly with the thiiranyl group, at least under selected conditions, include, for example, thiiranyl groups, aldehydes and ketones. Suitable reactive binder functional groups for reacting with the aldehydes and ketones include, for example, amines.

In some embodiments, the crosslinking agent is a cyclic acid anhydride, which effectively is at least bifunctional. Non-limiting examples of suitable cyclic acid anhydrides include, for example, 1,8-naphthalene dicarboxylic acid anhydride, itaconic anhydride, glutaric anhydride and citraconic anhydride, fumaric anhydride, phthalic anhydride, isophthalic anhydride, and terephthalic anhydride with maleic anhydride and phthalic anhydride being of particular interest.

The binder generally is capable of dispersing or dissolving the charge transport compound (in the case of the charge transport layer or a single layer construction) and/or the charge generating compound (in the case of the charge generating layer or a single layer construction). Examples of suitable binders for both the charge generating layer and charge transport layer generally include, for example, polystyrene-co-butadiene, polystyrene-co-acrylonitrile, modified acrylic polymers, polyvinyl acetate, styrene-alkyd resins, soya-alkyl resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly (hydroxyether) resins, polyhydroxystyrene resins, novolak, poly(phenylglycidyl ether)-co-dicyclopentadiene, copolymers of monomers used in the above-mentioned polymers, and combinations thereof. In some embodiments, the binder comprises a polymer with a reactive hydrogen functionality, such as hydroxyl, thiol, an amino group, a carboxyl group, or a combination thereof, that can react with the thiiranyl ring of the charge transport compounds of this invention or with a functional group of a crosslinking agent, such as a cyclic acid anhydride. In the organophotoreceptor, the functional group of the polymer can be bonded directly with the thiiranyl group or indirectly through a co-reactive crosslinking agent, for example, a cyclic acid anhydride group, to form the corresponding and predictable reaction product. Suitable binders with reactive functionality include, for example, polyvinyl butyral, such as BX-1 and BX-5 form Sekisui Chemical Co. Ltd., Japan.

Suitable optional additives for any one or more of the layers include, for example, antioxidants, coupling agents, dispersing agents, curing agents, surfactants, and combinations thereof.

The photoconductive element overall typically has a thickness from about 10 microns to about 45 microns. In the dual layer embodiments having a separate charge generating layer and a separate charge transport layer, charge generation layer generally has a thickness form about 0.5 microns to about 2 microns, and the charge transport layer has a thickness from about 5 microns to about 35 microns. In embodiments in which the charge transport material and the charge generating compound are in the same layer, the layer with the charge generating compound and the charge transport composition generally has a thickness from about 7 microns to about 30 microns. In embodiments with a distinct electron transport layer, the electron transport layer has an average thickness from about 0.5 microns to about 10 microns and in further embodiments from about 1 micron to about 3 microns. In general, an electron transport overcoat layer can increase mechanical abrasion resistance, increases resistance to carrier liquid and atmospheric moisture, and decreases degradation of the photoreceptor by corona gases. A person of ordinary skill in the art will recognize that additional ranges of thickness within the explicit ranges above are contemplated and are within the present disclosure.

Generally, for the organophotoreceptors described herein, the charge generation compound is in an amount from about 0.5 to about 25 weight percent, in further embodiments in an amount from about 1 to about 15 weight percent, and in other embodiments in an amount from about 2 to about 10 weight percent, based on the weight of the photoconductive layer. The charge transport material is in an amount from about 10 to about 80 weight percent, based on the weight of the photoconductive layer, in further embodiments in an amount from about 35 to about 60 weight percent, and in other embodiments from about 45 to about 55 weight percent, based on the weight of the photoconductive layer. The optional second charge transport material, when present, can be in an amount of at least about 2 weight percent, in other embodiments from about 2.5 to about 25 weight percent, based on the weight of the photoconductive layer, and in further embodiments in an amount from about 4 to about 20 weight percent, based on the weight of the photoconductive layer. The binder is in an amount from about 15 to about 80 weight percent, based on the weight of the photoconductive layer, and in further embodiments in an amount from about 20 to about 75 weight percent, based on the weight of the photoconductive layer. A person of ordinary skill in the art will recognize that additional ranges within the explicit ranges of compositions are contemplated and are within the present disclosure.

For the dual layer embodiments with a separate charge generating layer and a charge transport layer, the charge generation layer generally comprises a binder in an amount from about 10 to about 90 weight percent, in further embodiments from about 15 to about 80 weight percent and in some embodiments in an amount from about 20 to about 75 weight percent, based on the weight of the charge generation layer. The optional charge transport material in the charge generating layer, if present, generally can be in an amount of at least about 2.5 weight percent, in further embodiments from about 4 to about 30 weight percent and in other embodiments in an amount from about 10 to about 25 weight percent, based on the weight of the charge generating layer. The charge transport layer generally comprises a binder in an amount from about 20 weight percent to about 70 weight percent and in further embodiments in an amount from about 30 weight percent to about 50 weight percent. A person of ordinary skill in the art will recognize that additional ranges of binder concentrations for the dual layer embodiments within the explicit ranges above are contemplated and are within the present disclosure.

For the embodiments with a single layer having a charge generating compound and a charge transport material, the photoconductive layer generally comprises a binder, a charge transport material, and a charge generation compound. The charge generation compound can be in an amount from about 0.05 to about 25 weight percent and in further embodiment in an amount from about 2 to about 15 weight percent, based on the weight of the photoconductive layer. The charge transport material can be in an amount from about 10 to about 80 weight percent, in other embodiments from about 25 to about 65 weight percent, in additional embodiments from about 30 to about 60 weight percent and in further embodiments in an amount from about 35 to about 55 weight percent, based on the weight of the photoconductive layer, with the remainder of the photoconductive layer comprising the binder, and optional additives, such as any conventional additives. A single layer with a charge transport composition and a charge generating compound generally comprises a binder in an amount from about 10 weight percent to about 75 weight percent, in other embodiments from about 20 weight percent to about 60 weight percent, and in further embodiments from about 25 weight percent to about 50 weight percent. Optionally, the layer with the charge generating compound and the charge transport material may comprise a second charge transport material. The optional second charge transport material, if present, generally can be in an amount of at least about 2.5 weight percent, in further embodiments from about 4 to about 30 weight percent and in other embodiments in an amount from about 10 to about 25 weight percent, based on the weight of the photoconductive layer. A person of ordinary skill in the art will recognize that additional composition ranges within the explicit compositions ranges for the layers above are contemplated and are within the present disclosure.

In general, any layer with an electron transport compound can advantageously further include a UV light stabilizer. In particular, the electron transport layer generally can comprise an electron transport compound, a binder, and an optional UV light stabilizer. An overcoat layer comprising an electron transport compound is described further in copending U.S. patent application Ser. No. 10/396,536 to Zhu et al. entitled, "Organophotoreceptor With An Electron Transport Layer," incorporated herein by reference. For example, an electron transport compound as described above may be used in the release layer of the photoconductors described herein. The electron transport compound in an electron transport layer can be in an amount from about 10 to about 50 weight percent, and in other embodiments in an amount from about 20 to about 40 weight percent, based on the weight of the electron transport layer. A person of ordinary skill in the art will recognize that additional ranges of compositions within the explicit ranges are contemplated and are within the present disclosure.

The UV light stabilizer, if present, in any one or more appropriate layers of the photoconductor generally is in an amount from about 0.5 to about 25 weight percent and in some embodiments in an amount from about 1 to about 10 weight percent, based on the weight of the particular layer. A person of ordinary skill in the art will recognize that additional ranges of compositions within the explicit ranges are contemplated and are within the present disclosure.

For example, the photoconductive layer may be formed by dispersing or dissolving the components, such as one or more of a charge generating compound, the charge transport material of this invention, a second charge transport material such as a charge transport compound or an electron transport compound, a UV light stabilizer, and a polymeric binder in organic solvent, coating the dispersion and/or solution on the respective underlying layer and drying the coating. In particular, the components can be dispersed by high shear homogenization, ball-milling, attritor milling, high energy bead (sand) milling or other size reduction processes or mixing means known in the art for effecting particle size reduction in forming a dispersion.

The photoreceptor may optionally have one or more additional layers as well. An additional layer can be, for example, a sub-layer or an overcoat layer, such as a barrier layer, a release layer, a protective layer, or an adhesive layer. A release layer or a protective layer may form the uppermost layer of the photoconductor element. A barrier layer may be sandwiched between the release layer and the photoconductive element or used to overcoat the photoconductive element. The barrier layer provides protection from abrasion to the underlayers. An adhesive layer locates and improves the adhesion between a photoconductive element, a barrier layer, and a release layer, or any combination thereof. A sub-layer is a charge blocking layer and locates between the electrically conductive substrate and the photoconductive element. The sub-layer may also improve the adhesion between the electrically conductive substrate and the photoconductive element.

Suitable barrier layers include, for example, coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyvinyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above barrier layer polymers optionally may contain small inorganic particles such as fumed silica, silica, titania, alumina, zirconia, or a combination thereof. Barrier layers are described further in U.S. Pat. No. 6,001,522 to Woo et al., entitled "Barrier Layer For Photoconductor Elements Comprising An Organic Polymer And Silica," incorporated herein by reference. The release layer topcoat may comprise any release layer composition known in the art. In some embodiments, the release layer is a fluorinated polymer, siloxane polymer, fluorosilicone polymer, silane, polyethylene, polypropylene, polyacrylate, or a combination thereof The release layers can comprise crosslinked polymers.

The release layer may comprise, for example, any release layer composition known in the art. In some embodiments, the release layer comprises a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In further embodiments, the release layers comprise crosslinked polymers.

The protective layer can protect the organophotoreceptor from chemical and mechanical degradation. The protective layer may comprise any protective layer composition known in the art. In some embodiments, the protective layer is a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In some embodiments of particular interest, the release layers are crosslinked polymers.

An overcoat layer may comprise a charge transport material, such as an electron transport compound as described further in copending U.S. patent application Ser. No. 10/396,536, filed on Mar. 25, 2003 to Zhu et al. entitled, "Organoreceptor With An Electron Transport Layer," incorporated herein by reference. For example, an electron transport compound, as described above, may be used in the release layer of this invention. The electron transport compound in the overcoat layer can be in an amount from about 2 to about 50 weight percent, and in other embodiments in an amount from about 10 to about 40 weight percent, based on the weight of the release layer. A person of ordinary skill in the art will recognize that additional ranges of composition within the explicit ranges are contemplated and are within the present disclosure.

Generally, adhesive layers comprise a film forming polymer, such as polyester, polyvinylbutyral, polyvinylpyrrolidone, polyurethane, polymethyl methacrylate, poly(hydroxy amino ether) and the like. Barrier and adhesive layers are described further in U.S. Pat. No. 6,180,305 to Ackley et al., entitled "Organic Photoreceptors for Liquid Electrophotography," incorporated herein by reference.

Sub-layers can comprise, for example, polyvinylbutyral, organosilanes, hydrolyzable silanes, epoxy resins, polyesters, polyamides, polyurethanes, and the like. In some embodiments, the sub-layer has a dry thickness between about 20 Angstroms and about 2,000 Angstroms. Sublayers containing metal oxide conductive particles can be between about 1 and about 25 microns thick. A person of ordinary skill in the art will recognize that additional ranges of compositions and thickness within the explicit ranges are contemplated and are within the present disclosure.

The charge transport materials as described herein, and photoreceptors including these compounds, are suitable for use in an imaging process with either dry or liquid toner development. For example, any dry toners and liquid toners known in the art may be used in the process and the apparatus of this invention. Liquid toner development can be desirable because it offers the advantages of providing higher resolution images and requiring lower energy for image fixing compared to dry toners. Examples of suitable liquid toners are known in the art. Liquid toners generally comprise toner particles dispersed in a carrier liquid. The toner particles can comprise a colorant/pigment, a resin binder, and/or a charge director. In some embodiments of liquid toner, a resin to pigment ratio can be from 1:1 to 10:1, and in other embodiments, from 4:1 to 8:1. Liquid toners are described further in Published U.S. Patent Applications 2002/0128349, entitled "Liquid Inks Comprising A Stable Organosol," 2002/0086916, entitled "Liquid Inks Comprising Treated Colorant Particles," and 2002/0197552, entitled "Phase Change Developer For Liquid Electrophotography," all three of which are incorporated herein by reference.

Charge Transport Material

As described herein, an organophotoreceptor comprises a charge transport material having the formula

(1)

where $Y_1$ and $Y_2$ are, each independently, a bond, $—CR_1=N—NR_2—$, or $—CR_3=N—N=CR_4—$ where $R_1$, $R_2$, $R_3$, and $R_4$ comprise, each independently, H, an alkyl group, an alkenyl group, a heterocyclic group, or an aromatic group;

$X_1$ and $X_2$ are, each independently, a linking group having the formula $—(CH_2)_m—$, branched or linear, where m is an integer between 0 and 20, inclusive, and one or more of the methylene groups is optionally replaced by O, S, C=O, O=S=O, a heterocyclic group, an aromatic group, urethane, urea, an ester group, an $NR_5$ group, a $CHR_6$ group, or a $CR_7R_8$ group where $R_5$, $R_6$, $R_7$, and $R_8$ comprise, each independently, H, hydroxyl group, thiol group, an alkyl group, an alkenyl group, a heterocyclic group, or an aromatic group;

$T_1$ and $T_2$ are, each independently, a thiiranyl group, H, an alkyl group, an alkenyl group, or an aromatic group with the proviso that at least one of $T_1$ and $T_2$ is a thiiranyl group; and Ar comprises an aromatic group with the proviso that when both $Y_1$ and $Y_2$ are a bond and one of $T_1$ and $T_2$ is not a thiiranyl group, Ar comprises a bis[(N,N-disubstituted)amino]aromatic group or a bicarbazole group.

Specific, non-limiting examples of suitable charge transport materials within the general Formula (1) of the present invention have the following structures:

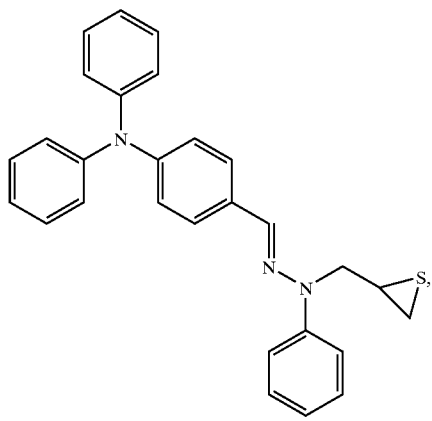
(2)
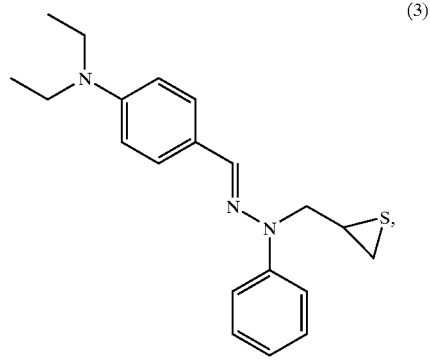
(3)
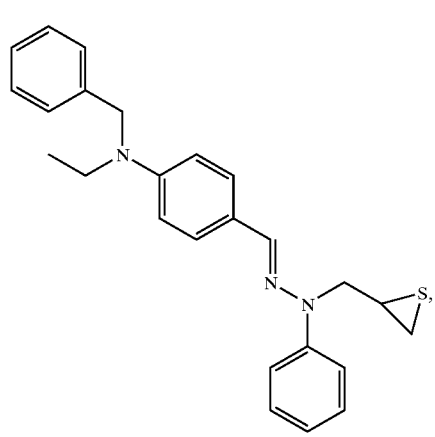
(4)
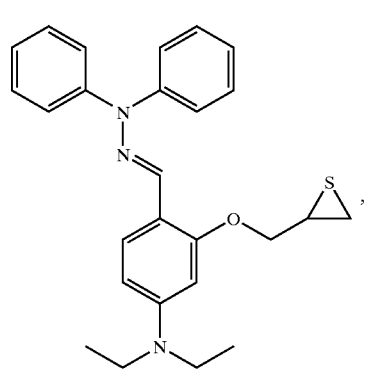
(5)
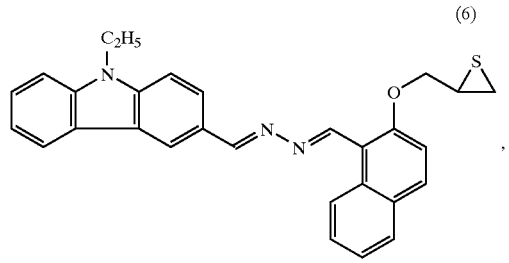
(6)
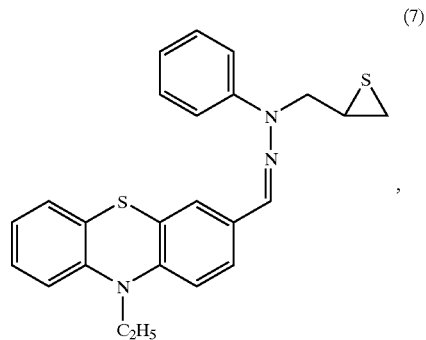
(7)
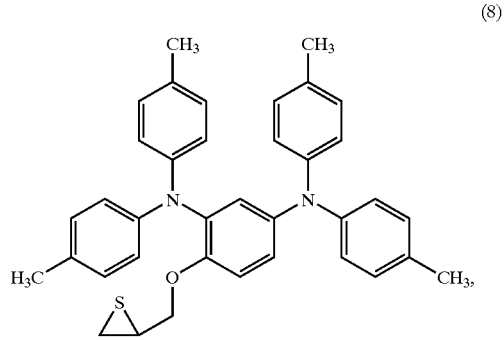
(8)
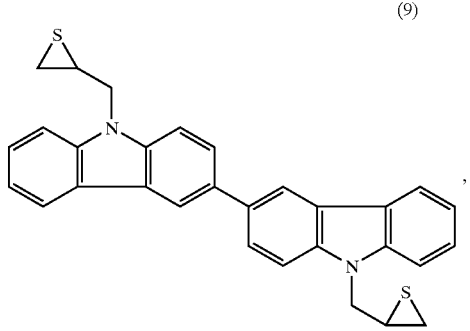
(9)

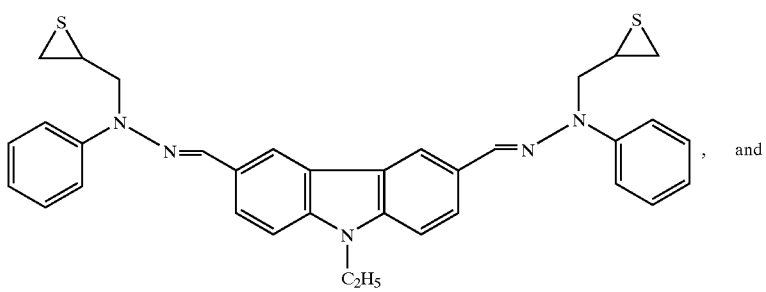

(10)

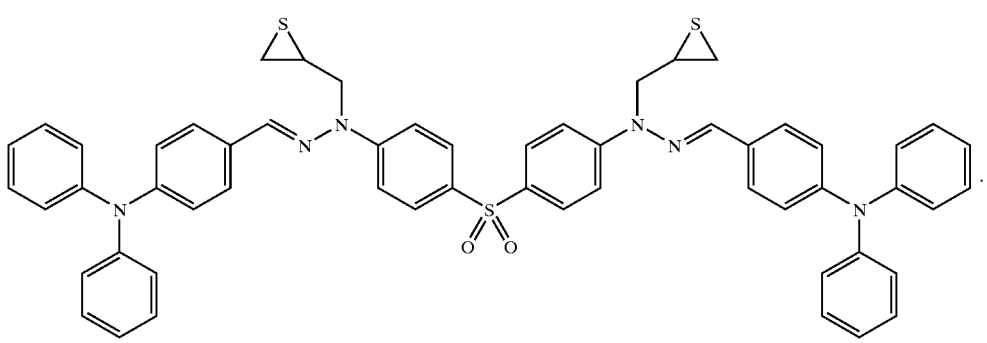

(11)

Synthesis of Charge Transport Materials

The synthesis of the charge transport materials of this invention can be prepared by the following multi-step synthetic procedure, although other suitable procedures can be used by a person of ordinary skill in the art based on the disclosure herein.

The first step is the synthesis of the epoxy analog of the targeted thiiranyl compound. The various preparations of suitable epoxy compounds for this invention have been disclosed in U.S. patent application Ser. Nos. 10/634,164, 10/695,581, 10/663,970, and 10/692,389, and U.S. Provisional Patent Application Nos. 60/444,001 and 60/459,150. All the above application references are incorporated herein by reference. In the next step, the epoxy compounds react with ammonium thiocyanate in refluxing tetrahydrofuran (THF) to provide the corresponding thiiranyl compound of this invention. The thiiranyl compound is isolated and purified.

In addition to the procedures in the paragraph above, some charge transport materials of this invention can be prepared by reacting at least one aromatic aldehyde with a dihydrazine to form a dihydrazone. The dihydrazone can then react with an organic halide comprising an epoxy group to form the corresponding epoxy compound. Non-limiting examples of suitable organic halide comprising an epoxy group for this invention are epihalohydrins, such as epichlorohydrin. The organic halide comprising an epoxy group can also be prepared by the epoxidation reaction of the corresponding organic halide having an olefin group. The epoxidation reaction is described in Carey et al., "Advanced Organic Chemistry, Part B: Reactions and Synthesis," New York, 1983, pp. 494–498, incorporated herein by reference. The organic halide having an olefin group can also be prepared by the Wittig reaction between a suitable organic halide having an aldehyde or keto group and a suitable Wittig reagent. The Wittig and related reactions are described in Carey et al., "Advanced Organic Chemistry, Part B: Reactions and Synthesis," New York, 1983, pp. 69–77, incorporated herein by reference. The epoxy compound then reacts with ammonium thiocyanate in refluxing tetrahydrofuran (THF) to provide the corresponding thiiranyl compound of this invention.

Some charge transport materials of this invention can also be prepared by reacting a bi-arylamine such as 3,3-bicarbazole with an organic halide comprising an epoxy group to form either a bi-arylamine with either one or two epoxy groups. The epoxy compound then reacts with ammonium thiocyanate in refluxing tetrahydrofuran (THF) to provide the corresponding thiiranyl compound of this invention.

The invention will now be described further by way of the following examples.

EXAMPLES

Example 1

Synthesis and Characterization Charge Transport Materials

This example described the synthesis and characterization of Compounds (2)–(11) in which the numbers refer to formula numbers above. The characterization involves chemical characterization, and the electronic characterization of materials formed with the compounds are described in subsequent examples.

9-Ethyl-3-carbazolecarboxaldehyde N-2,3-epoxypropyl-N-phenylhydrazone

A mixture of potassium hydroxide powder (KOH, 85%, 198 g, 3 mol,) and anhydrous sodium sulfate ($Na_2SO_4$, 51 g, 0.369 mol) was added in three stages to a mixture of 9-ethylcarbazol-3-carbazolecarboxaldehyde-N-phenylhydrazone (313.4 g, 1 mol) and epichlorohydrin (1.5 mol), while keeping the reaction mixture at 20–25° C.: stage quantities added were 33 g of $Na_2SO_4$ and 66 g of KOH initially; 9.9 g of $Na_2SO_4$ and 66 g of KOH after 1 hour of reaction; and 9.9 g of $Na_2SO_4$ and 66 g of KOH after 2 hours of reaction. The reaction mixture was stirred vigorously at 35–40 °C. until the starting hydrazone disappeared (approximately 3–4 hours). Subsequently, the mixture was cooled to room temperature and any remaining solids were removed by filtration. The liquid organic phase was treated with diethyl ether and washed with distilled water until the washed water was of a neutral pH. The organic layer was dried over anhydrous magnesium sulfate, treated with activated charcoal, and filtered. The solvent and excess epichlorohydrin were removed by evaporation in a rotory evaporator. The residue was recrystallized from a mixture of toluene and 2-propanol in a 1:1 ratio by volume. The crystals formed upon standing were filtered off and washed with 2-propanol to give 290 g of product (78.5% yield). The melting point was found to be 136–137° C. (recrystallized from toluene). The $^1$H NMR spectrum (250 MHz) of the product in CDCl$_3$ was characterized by the following chemical shifts ($\delta$, ppm): 8.35 (s, 1H, 4-H$_{Ht}$); 8.14 (d, J=7.8 Hz, 1H, 1-H$_{Ht}$); 7.93 (d, J=7.6 Hz, 1H, 2-H$_{Ht}$); 7.90 (s, 1H, CH=N); 7.54–7.20 (m, 8H, Ph, Ht); 6.96 (t, J=7.2 Hz, 1H, 4-H$_{Ph}$); 4.37 (m, 3H, CH$_2$CH$_3$, one of the NCH$_2$ protons); 4.04 (dd, J$_1$=4.3 Hz, J$_2$=16.4 Hz, 1H, next of the NCH$_2$ protons); 3.32 (m, 1H, CH); 2.88 (dd, 1H, part of the ABX system, cis-H$_A$ of CH$_2$O, J$_{AX}$=2.6 Hz, J$_{AB}$=4.9 Hz); 2.69 (dd, 1H, part of the ABX system, trans-H$_B$ of CH$_2$O, J$_{BX}$=4.0 Hz); and 1.44 (t, J=7.2 Hz, 3H, CH$_3$). An elemental analysis yielded the following results in weight percent C, 78.32; H, 6.41; and N, 11.55; which compared with calculated values for C$_{24}$H$_{23}$N$_3$O in weight percent of C, 78.02; H, 6.28; and N, 11.37.

4-(Diphenylamino)benzaldehyde N-2,3-epoxypropyl-N-phenylhydrazone 4-(Diphenylamino)benzaldehyde N-2,3-epoxypropyl-N-phenylhydrazone was prepared according to the preparation procedure above for 9-ethyl-3-carbazolecarboxaldehyde N-2,3-epoxypropyl-N-phenylhydrazone except that 9-ethyl-3-carbazolecarboxaldehyde-N-phenylhydrazone was replaced by 4-(diphenylamino)benzaldehyde-N-phenylhydrazone (1 mol). The yield of 4-(diphenylamino)benzaldehyde N-2,3-epoxypropyl-N-phenylhydrazone was 377.1 g (89.9%). The melting point was found to be 141–142.5° C. (recrystallized from toluene). The $^1$H NMR spectrum (250 MHz) of the product in CDCl$_3$ was characterized by the following chemical shifts ($\delta$, ppm): 7.65–6.98 (m, 19H, CH=N, Ar); 6.93 (t, J=7.2 Hz, 1H, 4-H$_{Ph}$); 4.35 (dd, 1H, part of the ABX system, H$_A$ of NCH$_2$, J$_{AX}$=2.4 Hz, J$_{AB}$=16.4); 3.99 (dd, 1H, part of the ABX system, H$_B$ of NCH$_2$, J$_{BX}$=4.1 Hz); 3.26 (m, 1H, CH); 2.84 (dd, 1H, part of the ABX system, cis-H$_A$ of CH$_2$O, J$_{AX}$=2.7 Hz, J$_{AB}$=4.8 Hz); and 2.62 (dd, 1H, part of the ABX system, trans-HB of CH$_2$O, J$_{BX}$=4.1 Hz). An elemental analysis yielded the following results in weight percent C, 80.02; H, 6.31; and N, 9.91; which compared with calculated values for C$_{28}$H$_{25}$N$_3$O in weight percent of C, 80.16; H, 6.01; and N, 10.02.

4-Diethylaminobenzaldehyde N-2,3-epoxypropyl-N-phenylhydrazone

A mixture of potassium hydroxide powder (KOH, 85%, 198 g, 3 mol,) and anhydrous sodium sulfate (Na$_2$SO$_4$, 51 g, 0.369 mol) was added in three stages to a mixture of 4-(diethylamino)benzaldehyde N-phenylhydrazone (267.4 g, 1 mol) and epichlorohydrin (1.5 mol), while keeping the reaction mixture at 20–25° C.: stage quantities added were 33 g of Na$_2$SO$_4$ and 66 g of KOH initially; 9.9 g of Na$_2$SO$_4$ and 66 g of KOH after 1 hour of reaction; and 9.9 g of Na$_2$SO$_4$ and 66 g of KOH after 2 hours of reaction. The reaction mixture was stirred vigorously at 35–40° C. until the starting hydrazone disappeared (approx. 4–5 hours). Subsequently, the mixture was cooled to room temperature, and the solids were removed by filtration. The liquid organic phase was treated with diethyl ether and washed with distilled water until the washed water was neutral. The organic layer was dried over anhydrous magnesium sulfate, treated with activated charcoal, and filtered. The solvent and excess epichlorohydrin were removed by evaporation in a rotory evaporator. The residue was recrystallized from diethyl ether and the crystals that formed upon standing were filtered off and washed with 2-propanol to give 260 g of the product (80.4% yield). The melting point was found to be 79–80.5° C. (recrystallized from diethyl ether). The $^1$H NMR spectrum (250 MHz) of the product in CDCl$_3$ was characterized by the following chemical shifts ($\delta$, ppm): 7.7–6.7 (m, 8H, Ar, CH=N); 6.6 (d, 2H, 2-H, 6-H of p-Ph); 4.4–3.6 (m, 2H, NCH$_2$CH); 3.6–3.0 (m, 5H, CH$_2$CH$_3$, CH$_2$CHCH$_2$); 2.75 (m, 1H, ABX, cis-H$_A$ of CH$_2$O) 2.55 (m, ABX, trans-H$_B$ of CH$_2$O); and 1.1 (t, J=7.0 Hz, 6H, CH$_3$).

4-(N-ethyl-N-benzylamino)benzaldehyde N-2,3-epoxypropyl-N-phenylhydrazone 4-(N-ethyl-N-benzylamino)benzaldehyde N-2,3-epoxypropyl-N-phenylhydrazone was made similarly to 9-ethyl-3-carbazolecarboxaldehyde N-2,3-epoxypropyl-N-phenylhydrazone except that N-ethyl-N-benzylaminobenzaldehyde (329.4 g, 1 mol) replaced 9-ethyl-3-cabazolecarboxaldehyde. The epoxide was isolated by analogy to N-ethyl-3-carbazolecarboxaldehyde N-2,3-epoxypropyl-N-phenylhydrazone except that column chromatography (using silica gel, grade 62, 60–200 mesh, 150 Angstrom, obtained from Aldrich) using a mixture of ether and hexane in a 1:2 ratio by volume as eluant was used as an additional purification step. The solvent was removed by evaporation in a rotory evaporator to yield an oily 4-(N-ethyl-N-benzylamino)benzaldehyde N-2,3-epoxypropyl-N-phenylhydrazone (310 g, 80.4% yield). The $^1$H NMR spectrum (400 MHz) of the product in CDCl$_3$ was characterized by the following chemical shifts ($\delta$, ppm): 7.70 (s, 1H, CH=N); 7.55 (d, 2H, J=8.8 Hz, 2,6-H$_{p-Ph}$); 7.16–7.41 (m, 4H, Ar); 6.93 (t, 1H, J=7.3 Hz, 4-H$_{Ph}$); 6.69 (d, 2H, J=8.8 Hz, 3,5-H $_{p-Ph}$); 4.58 (s, 2H, CH$_2$Ph); 4.37 (dd, 1H, ABX, J$_{AB}$=16.2, J$_{AX}$=2.4 Hz, H$_A$ of NCH$_2$); 3.99 (dd, 1H, ABX, J$_{BX}$=4.1 Hz, H$_B$ of NCH$_2$); 3.28 (m, 1H, CH$_X$); 3.53 (q, 2H, J=7.3 Hz, CH$_2$CH$_3$); 2.84 (dd, 1H, ABX, J$_{AB}$=4.8 Hz, J$_{AX}$=2.7 Hz, cis-H$_A$ of CH$_2$O); 2.62 (dd, 1H, ABX, J$_{BX}$=4.0 Hz, trans-H$_B$ of CH$_2$O); and 1.24 (t, J=7.3 Hz, 3H, CH$_2$CH$_3$).

Compound (2)

4-(Diphenylamino)benzaldehyde-N-(2,3-epoxypropyl)-N-phenylhydrazone (17 g, 40.5 mmole), ammonium thiocyanate (10 g, 0.13 mole , obtained from Aldrich), and 40 ml of tetrahydrofuran (THF) were added to a 100 ml, 3-neck round bottom flask equipped with a reflux condenser and a magnetic stirrer. The mixture was refluxed for 2 hours. The solvent was removed by evaporation, and the residue was subjected to liquid chromatography (using silica gel, grade 62, 60–200 mesh, 150 Angstrom, obtained from Aldrich) using a mixture of acetone and hexane in a 1:4 ratio by volume as eluant. Fractions containing the product were collected, and the solvent was evaporated. The residue was recrystallized from benzene. The solid was filtered off and washed with isopropanol. The yield was 12 g (68%). The $^1$H NMR spectrum (100 MHz) of the product in CDCl$_3$ was characterized by the following chemical shifts ($\delta$, ppm): 7.54 (s, 1H, CH=N); 7.50–6.90 (m, 19H, Ar); 5.06 (p, 1H, CH); 4.19 (d, 2H, NCH$_2$); and 3.72–3.32 (m, 2H, SCH$_2$). An elemental analysis yielded the following results in weight percent C, 77.12; H, 5.66; and N, 9.49; which compared with calculated values for C$_{28}$H$_{25}$N$_3$S in weight percent of C, 77.21; H, 5.79; and N, 9.65.

Compound (3)

4-(Diethylamino)benzaldehyde-N-(2,3-epoxypropyl)-N-phenylhydrazone (13.2 g, 40.5 mmole), ammonium thiocyanate (10 g, 0.13 mole, obtained from Aldrich), and 40 ml of tetrahydrofuran (THF) were added to a 100 ml, 3-neck round bottom flask equipped with a reflux condenser and a magnetic stirrer. The mixture was refluxed for 2 hours. The solvent was removed by evaporation and the residue was subjected to liquid chromatography (using silica gel, grade 62, 60–200 mesh, 150 Angstrom, obtained from Aldrich) using a mixture of acetone and hexane in a 1:4 ratio by volume as eluant. Fractions containing the product were combined, and the solvent was evaporated. Diethyl ether was added to the oily residue to make a 20 weight % product solution in ether. The ether solution was poured with intensive stirring into a 10-fold excess of ethanol. The solid product that formed was filtered off and dried in vacuum oven at 50° C. for 8 hours. The yield was 7.2 g (52%). The $^1$H NMR spectrum (400 MHz) of the product in CDCl$_3$ was characterized by the following chemical shifts (δ, ppm): 7.72 (s, 1H, CH=N); 7.58 (d, J=8.8 Hz, 2H, 2,6-H of p-Ph); 7.41–7.28 (m, 4H, Ar); 6.93 (dd, 1H, 4-H Ph); 6.69 (d, J=8.8 Hz, 2H, 3,5-H of p-Ph); 4.25 (dd,1H, ABX, one (H$_A$) of NCH$_2$, J$_{AB}$=16.1 Hz, J$_{AX}$=6.6 Hz); 4.05 (dd, 1H, ABX, one (H$_B$) of NCH$_2$, J$_{BX}$=5.1 Hz); 3.39 (q, J=7.3 Hz, 4H, CH$_2$CH$_3$); 3.19 (p, 1H, J=5.9 Hz, CHS); 2.55 (dd, 1H, ABX, trans proton (H$_B$) of SCH$_2$, J$_{AB}$=1.3 Hz, J$_{BX}$=5.9 Hz); 2.39 (dd, 1H, ABX, cis proton (H$_A$), SCH$_2$, J$_{AX}$=5.0 Hz); and 1.19 (t, J=7.3 Hz, 3H, CH$_3$). An elemental analysis yielded the following results in weight percent C, 74.64; H, 5.96; and N, 10.99; which compared with calculated values for C$_{20}$H$_{25}$N$_3$S in weight percent of C, 70.76; H, 7.42; and N, 9.44.

Compound (4)

4-(N-Benzyl-N-ethylamino)benzaldehyde-N-(2,3-epoxypropyl)-N-phenylhydrazone (15.7 g, 40.5 mmole), ammonium thiocyanate (10 g, 0.13 mole, obtained from Aldrich), and 40 ml of tetrahydrofuran (THF) were added to a 100 ml, 3-neck round bottom flask equipped with a reflux condenser and a magnetic stirrer. The mixture was refluxed for 2 hours. The solvent was removed by evaporation, and the residue was subjected to liquid chromatography (using silica gel, grade 62, 60–200 mesh, 150 Angstrom, obtained from Aldrich) using a mixture of acetone and hexane in a 1:4 ratio by volume as eluant. Fractions containing the product were combined, and the solvent was evaporated. The yield of the oily product was 11.4 g (70%). The $^1$H NMR spectrum (400 MHz) of the product in CDCl$_3$ was characterized by the following chemical shifts (δ, ppm): 7.70 (s, 1H, CH=N); 7.55 (d, J=8.8 Hz, 2H, 2,6-H of p-Ph); 7.41–7.16 (m, 4H, Ar); 6.93 (dd, 1H, 4-H Ph); 6.69 (d, J=8.8 Hz, 2H, 3,5-H of p-Ph); 4.58 (s, 2H, CH$_2$Ph); 4.24 (dd, 1H, ABX, one (H$_A$) of NCH$_2$, J$_{AB}$=16.1 Hz, J$_{AX}$=6.6 Hz); 4.05 (dd, 1H, ABX, one (H$_B$) of NCH$_2$, J$_{BX}$=5.1 Hz); 3.53 (q, J=7.3 Hz, 4H, CH$_2$CH$_3$); 3.18 (p, 1H, J=5.9 Hz, CHS); 2.54 (dd, 1H, ABX, trans proton (H$_B$) of SCH$_2$, J$_{AB}$=1.3 Hz, J$_{BX}$=5.9 Hz); 2.38 (dd, 1H, ABX, cis proton (H$_A$), SCH$_2$, J$_{AX}$=5.0 Hz); and 1.24 (t, J=7.3 Hz, 3H, CH$_3$). An elemental analysis yielded the following results in weight percent: C, 74.64; H, 6.66; N, 10.39; which compared with calculated values for C$_{25}$H$_{27}$N$_3$S in weight percent of: C, 74.77; H, 6.78; N, 10.46.

Compound (5)

Compound (5) can be prepared according to the preparation procedure for Compound (2) except that 4-(diphenylamino)benzaldehyde-N-(2,3-epoxypropyl)-N-phenylhydrazone is replaced with Compound (2) of U.S. Provisional Patent Application No. 60/444,001, incorporated herein by reference.

Compound (6)

Compound (6) can be prepared according to the preparation procedure for Compound (2) except that 4-(diphenylamino)benzaldehyde-N-(2,3-epoxypropyl)-N-phenylhydrazone is replaced with Compound (2) of U.S. patent application Ser. No. 10/663,970, incorporated herein by reference.

Compound (7)

Compound (7) can be prepared according to the preparation procedure for Compound (2) except that 4-(diphenylamino)benzaldehyde-N-(2,3-epoxypropyl)-N-phenylhydrazone is replaced with Compound (2) of U.S. patent application Ser. No. 10/695,581, incorporated herein by reference.

Compound (8)

Compound (8) can be prepared according to the preparation procedure for Compound (2) except that 4-(diphenylamino)benzaldehyde-N-(2,3-epoxypropyl)-N-phenylhydrazone is replaced with Compound (2) of U.S. patent application Ser. No. 10/692,389, incorporated herein by reference.

Compound (9)

9-(2,3-Epoxy-propyl)carbazole (2.2 g, 0.01 mol., obtained from BIOLAR, str. Rupnicu 3, Olaine LV-2114, Latvia), 80 ml of chloroform, and, after dissolution, anhydrous ferric chloride (FeCl$_3$, 6.5 g, 0.04 mol, obtained from Aldrich) were added to a 100 ml, 3-neck round bottom flask equipped with a reflux condenser and a magnetic stirrer. The reaction mixture was intensively stirred under argon atmosphere at room temperature until 9-(2,3-epoxypropyl)carbazole completely reacted (20 minutes, as determined by thin layer chromatography using a mixture of acetone and hexane in a ratio of 7:18 by volume as the mobile phase). The reaction mixture was diluted with 150 ml of acetone, treated with 250 ml of ethyl acetate, washed three times with HCl solution (0.5 M, 100 ml), and washed with distilled water until the wash water was neutral. The organic layer was dried over anhydrous MgSO$_4$, treated with activated charcoal, and filtered. Then, the solvents were removed by evaporation. The crude product was recrystallized from toluene and washed repeatedly with 2-propanol to afford 2.07 g (80.4% yield) of the 9-(3-chloro-2-hydroxypropyl)-3,3'-bicarbazyle. The product had a melting point of 152–153° C. (recrystallized from toluene). The IR spectrum of the product in a KBr salt window displayed the following characteristic bonds, v (cm$^{-1}$): 3642–3071 (OH), 3042, 3028 (CH$_{Ar}$), and 2942, 2914 (CH$_{Al}$). The $^1$H NMR spectrum (250 MHz) of the product in CDCl$_3$ was characterized by the following chemical shifts (δ, ppm): 8.37 (s, 2H, 5-H$_{Ht}$); 8.17 (d, J=7.8 Hz, 2H, 4-H$_{Ht}$); 7.80 (d, J=8.4 Hz, 2H, 6-H$_{Ht}$); 7.70–7.1 (m, 8H, Ht); 4.46 (m, 6H, NCH$_2$, CHOH); 3.73–3.63 (dd, 2H, one of CH$_2$Cl protons, H$_A$, J$_{AX}$=5.0 Hz, J$_{AB}$=11.4 Hz); 3.63–3.53 (dd, 2H, another of CH$_2$Cl protons, H$_B$, J$_{BX}$=4.6 Hz); and 2.40 (s, 2H, OH). An elemental analysis yielded the following results in weight percent C, 69.52; H, 5.11; and N, 5.43; which compared with calculated values for $C_{30}H_{24}N_2O_2$ in weight percent of C, 69.64; H, 5.06; and N, 5.41.

9-(3-Chloro-2-hydroxypopyl)-3,3'-bicarbazyle (3.0 g, 5.8 mmol), 60 ml of 1,4-dioxane, and, after dissolution, powdered potassium hydroxide (85%, 2.3 g, 34.8 mmol) were added to a 100 ml, 3-neck round bottom flask equipped with a reflux condenser and a magnetic stirrer. The reaction mixture was stirred intensively for 30 minutes until the reaction was completed (as determined by thin layer chromatography using a mixture of acetone and hexane in a ratio of 7:18 by volume as the mobile phase), and then the mixture was filtered to remove any solids. The liquid organic phase was treated with ethyl acetate and washed with distilled water until the wash water was neutral. The organic layer was dried over anhydrous $MgSO_4$, and the solvent removed by evaporation.

The residue was recrystallized from toluene, The crystals were harvested by filtration, washed repeatedly with 2-propanol, and dried under vacuum. The yield of 9-(2,3-epoxypropyl)-3,3'-bicarbazyle was 2.1 g (81.4%), and the product had a melting point of 173.5–175.5° C. (recrystallized from toluene). The IR spectrum of the product in a KBr salt window displayed the following characteristic bonds, ν (cm$^{-1}$): 3071, 3042 ($CH_{Ar}$); 2971, 2942 ($CH_{Al}$); 1256, 1218, 855, 801, 794 (epoxy ring). The $^1H$ NMR spectrum (250 MHz) of the product in $CDCl_3$ was characterized by the following chemical shifts (δ, ppm): 8.39 (s, 2H, 5-$H_{Ht}$); 8.17 (d, J=7.9 Hz, 2H, 4-$H_{Ht}$); 7.82 (d, J=8.5 Hz, 2H, 6-$H_{Ht}$); 7.70–7.1 (m, 8H, Ht); 4.70–4.60 (dd, 2H, one of $NCH_2$ protons, $H_A$, $J_{AX}$=3.2 Hz, $J_{AB}$=15.8 Hz); 4.50–4.33 (dd, 2H, another of $NCH_2$ protons, $H_B$, $J_{BX}$=4.7 Hz); 3.38 (m, 2H, CH); 2.82 (dd, 2H, one of $OCH_2$ protons, $H_A$, $J_{AX}$=4.3 Hz, $J_{AB}$=4.8 Hz); and 2.65–2.55 (dd, 2H another of $OCH_2$ protons, $H_B$, $J_{BX}$=2.7 Hz). An elemental analysis yielded the following results in weight percent C, 80.89; H, 5.48; and N, 6.11; which compared with calculated values for $C_{30}H_{24}N_2O_2$ in weight percent of C, 81.06; H, 5.44; and N, 6.03.

Compound (9) can be prepared by adding 9-(2,3-Epoxypropyl)-3,3'-bicarbazyle (9 g, 20.25 mmole), ammonium thiocyanate (5 g, 65 mmole, obtained from Aldrich) and 20 ml of tetrahydrofuran (THF) to a 50 ml 3-neck round bottom flask equipped with a reflux condenser and a magnetic stirrer. The mixture is refluxed for 2 hours. The solvent is evaporated and the product is purified by liquid chromatography.

Compound (10)

Compound (10) can be prepared according to the preparation procedure for Compound (2) except that 4-(diphenylamino)benzaldehyde-N-(2,3-epoxypropyl)-N-phenylhydrazone is replaced with Compound (9) of U.S. patent application Ser. No. 10/634164, incorporated herein by reference.

Compound (11)

4,4'-Dichlorodiphenyl sulfone (20 g, 0.069 mol, obtained from Aldrich) and hydrazine monohydrate (98%, 158 ml, obtained from Aldrich) were added to a 250 ml 3-neck round bottom flask equipped with a reflux condenser and a magnetic stirrer. The suspension was refluxed for 24 hours and then cooled to room temperature. The crystals that formed upon standing were collected by filtration, washed 3 times with water, and once with isopropanol. The yield of 4,4'-dihydrazinodiphenyl sulfone was 15.75 g (81.8%). The product had a melting point of 193–194° C.

4-(diphenylamino)benzaldehyde (25 g, 0.09 mol, obtained from Aldrich) and 4,4'-dihydrazinodiphenyl sulfone (11.37 g, 0.041 mol) dissolved in 80 ml of dioxane were added to a 250 ml round bottom flask equipped with a reflux condenser and magnetic stirrer. The reaction mixture was heated to 50° C. and stirred intensively for 2 h. The solution was distilled to obtain 30.1 g (93.4% yield) of 4,4'-dihydrazondiphenyl sulfone.

4,4'-dihydrazondiphenyl sulfone (30.1 g 0.038 mol) and epichlorohydrin (68 ml, 0.855 mol, obtained from Aldrich) were added to a 250 ml 3-neck round bottom flask equipped with a reflux condenser, thermometer, and magnetic stirrer. The reaction mixture was stirred vigorously at 35–40° C. for 7 hours, during which time powdered potassium hydroxide (85%, 11.3 g, 0.171 mol) and anhydrous $Na_2SO_4$ (2.9 g, 0.0228 mol) were added in three portions with prior cooling of the reaction mixture to 20–25° C. Upon completion of the reaction, the mixture was cooled to room temperature, and solids were removed by filtration. The liquid organic phase was treated with ethyl acetate and washed with distilled water until the wash water was neutral. The organic layer was then dried over anhydrous magnesium sulfate, treated with activated charcoal, filtered, and solvents were removed by evaporation. The di-epoxy compound was purified by column chromatography (silica gel, grade 62, 60–200 mesh, 150 Å, Aldrich) using 1:4 acetone:hexane as the eluant to obtain 19.3 g (56% yield) of the diepoxide of 4,4'-dihydrazondiphenyl sulfone. The melting point was found to be 223–225° C. (recrystallized from a mixture of acetone and hexane in a ratio of 1:4,). The $^1H$ NMR spectrum (100 MHz) of the product in $CDCl_3$ was characterized by the following chemical shifts (δ, ppm): 8.0–6.8 (m, 38H, CH=N, Ar); 4.5–4.3 (dd, 2H, one proton of $NCH_2$); 4.1–3.8 (dd, 2H, another proton of $NCH_2$); 3.2 (m, 2H, CH); 2.9–2.8 (dd, 2H, one proton of $OCH_2$); and 2.7–2.5 (dd, another proton of $OCH_2$). An elemental analysis yielded the following results in weight percent: C, 74.71; H, 5.33; and N, 9.45; which compared with calculated values for $C_{38}H_{35}N_5O_2$ in weight percent of C, 74.64; H, 5.37; and N, 9.33.

Compound (11) can be prepared by adding diepoxide of 4,4'-dihydrazondiphenyl sulfone (36.5 g, 40.5 mmole), ammonium thiocyanate (10 g, 0.13 mole, obtained from Aldrich) and 40 ml of tetrahydrofuran (THF) to a 100 ml 3 neck round bottom flask equipped with a reflux condenser and a magnetic stirrer. The mixture is refluxed for 2 hours. The solvent is evaporated, and the product is purified by liquid chromatography.

Example 2

Charge Mobility Measurements

This example describes the measurement of charge mobility for charge transport materials, specifically Compound (2) as described above.

Sample 1

Sample 1 was prepared by dissolving a mixture of 0.1 g of the Compound (2) and 0.1 g of polyvinylbutyral (S-LEC B BX-1, commercially obtained from Sekisui) in 2 ml of tetrahydrofuran. The solution was coated on a polyester film with conductive aluminum layer by a dip roller. After the coating was dried for 1 hour at 80° C., a clear 10 μm thick layer was formed. The hole mobility of the sample was measured and the results are presented in Table 1.

Sample 2

Sample 2 was prepared and tested similarly as Sample 1, except polycarbonate Z-200 (from Mitsubishi Gas Chemical) was used instead of polyvinylbutyral.

Mobility Measurements

Each sample was corona charged positively up to a surface potential U and illuminated with 2 ns long nitrogen laser light pulse. The hole mobility p was determined as described in Kalade et al., "Investigation of charge carrier transfer in electrophotographic layers of chalkogenide glasses," Proceeding IPCS 1994: The Physics and Chemistry of Imaging Systems, Rochester, N.Y., pp. 747–752, incorporated herein by reference. The hole mobility measurement was repeated with changes to the charging regime to charge the sample to different U values, which corresponded to different electric field strength, E, inside the layer. This dependence on electric field strength was approximated by the formula $$\mu = \mu_0 e^{\alpha\sqrt{E}}$$

Here E is electric field strength, $\mu_0$ is the zero field mobility and $\alpha$ is Pool-Frenkel parameter. Table 1 lists the mobility characterizing parameters $\mu_0$ and $\alpha$ values and the mobility value at the $6.4 \times 10^5$ V/cm field strength as determined from these measurements.

TABLE 1

| Sample | $\mu_0$ (cm$^2$/V·s) | $\mu$ (cm$^2$/V·s) at $6.4 \cdot 10^5$ V/cm | $\alpha$ (cm/V)$^{0.5}$ | Ionization Potential (eV) |
|---|---|---|---|---|
| Sample 1 (Compound 2) | $8 \times 10^{-10}$ | $4.7 \times 10^{-9}$ | 0.0022 | 5.48 |
| Sample 2 (Compound 2) | $3 \times 10^{-8}$ | $2.2 \times 10^{-6}$ | 0.0054 | |

Example 3

Ionization Potential Measurements

This example describes the measurement of the ionization potential for the charge transport materials, specifically Compound (2) described in Example 1.

To perform the ionization potential measurements, a thin layer of charge transport material about 0.5 µm thickness was coated from a solution of 2 mg of charge transport material in 0.2 ml of tetrahydrofuran on a 20 cm$^2$ substrate surface. The substrate was polyester film with an aluminum layer over a methylcellulose sublayer of about 0.4 µm thickness.

Ionization potential was measured as described in Grigalevicius et al., "3,6-Di(N-diphenylamino)-9-phenylcarbazole and its methyl-substituted derivative as novel hole-transporting amorphous molecular materials," Synthetic Metals 128 (2002), p. 127–131, incorporated herein by reference. In particular, each sample was illuminated with monochromatic light from the quartz monochromator with a deuterium lamp source. The power of the incident light beam was 2–5·10$^{-8}$ W. A negative voltage of –300 V was supplied to the sample substrate. A counter-electrode with the 4.5×15 mm$^2$ slit for illumination was placed at 8 mm distance from the sample surface. The counter-electrode was connected to the input of a BK2-16 type electrometer, working in the open input regime, for the photocurrent measurement. A $10^{-15}$–$10^{-12}$ amp photocurrent was flowing in the circuit under illumination. The photocurrent, I, was strongly dependent on the incident light photon energy hv. The $I^{0.5}$=f(hv) dependence was plotted. Usually, the dependence of the square root of photocurrent on incident light quanta energy is well described by linear relationship near the threshold (see references "Ionization Potential of Organic Pigment Film by Atmospheric Photoelectron Emission Analysis," Electrophotography, 28, Nr. 4, p. 364 (1989) by E. Miyamoto, Y. Yamaguchi, and M. Yokoyama; and "Photoemission in Solids," Topics in Applied Physics, 26, 1–103 (1978) by M. Cordona and L. Ley, both of which are incorporated herein by reference). The linear part of this dependence was extrapolated to the hv axis, and the Ip value was determined as the photon energy at the interception point. The ionization potential measurement has an error of ±0.03 eV. Table 1 lists the ionization potential value of Compound (2).

As understood by those skilled in the art, additional substitution, variation among substituents, and alternative methods of synthesis and use may be practiced within the scope and intent of the present disclosure of the invention. The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

What is claimed is:

1. An organophotoreceptor comprising an electrically conductive substrate and a photoconductive element on the electrically conductive substrate, the photoconductive element comprising:

(a) a charge transport material having the formula

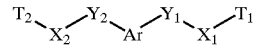

where $Y_1$ and $Y_2$ are, each independently, a bond, —CR$_1$=N—NR$_2$—, or —CR$_3$=N—N=CR$_4$— where $R_1$, $R_2$, $R_3$, and $R_4$ comprise, each independently, H, an alkyl group, an alkenyl group, a heterocyclic group, or an aromatic group;

$X_1$ and $X_2$ are, each independently, a linking group having the formula —(CH$_2$)$_m$—, branched or linear, where m is an integer between 0 and 20, inclusive, and one or more of the methylene groups is optionally replaced by O, S, C=O, O=S=O, a heterocyclic group, an aromatic group, urethane, urea, an ester group, an NR$_5$ group, a CHR$_6$ group, or a CR$_7$R$_8$ group where R$_5$, R$_6$, R$_7$, and R$_8$ comprise, each independently, H, hydroxyl group, thiol group, an alkyl group, an alkenyl group, a heterocyclic group, or an aromatic group;

$T_1$ and $T_2$ are, each independently, a thiiranyl group, H, an alkyl group, an alkenyl group, or an aromatic group with the proviso that at least one of $T_1$ and $T_2$ is a thiiranyl group; and Ar comprises an aromatic group with the proviso that when both $Y_1$ and $Y_2$ are a bond and one of $T_1$ and $T_2$ is not a thiiranyl group, Ar comprises a bis[(N,N-disubstituted)amino]aromatic group or a bicarbazole group; and (b) a charge generating compound.

2. An organophotoreceptor according to claim 1 wherein $T_2$ is H, the m value for $X_2$ is 0, $Y_2$ is a bond, $Y_1$, is —$CR_1$=N—$NR_2$— where the C atom is connected to Ar and the terminal N atom is connected to $X_1$, and $T_1$ comprises a thiiranyl group.

3. An organophotoreceptor according to claim 2 wherein Ar comprises an arylamine group or an aromatic heterocyclic group.

4. An organophotoreceptor according to claim 2 wherein $R_2$ comprises an aromatic group.

5. An organophotoreceptor according to claim 4 wherein the aromatic group of $R_2$ has the formula

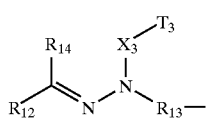

where $R_{12}$ comprises an arylamine group, $R_{13}$ is a linking group comprising an alkyl group, an alkenyl group, or an aryl group, $R_{14}$ comprises H, an alkyl group, an alkenyl group, or an aryl group, $X_3$ has the formula —$(CH_2)_m$—, branched or linear, where m is an integer between 1 and 20, and $T_3$ is a thiiranyl group.

6. An organophotoreceptor according to claim 1 wherein the m value for $X_1$ is 0, $T_1$ comprises an aromatic group, $T_2$ comprises a thiiranyl group, $Y_2$ is a bond, and $Y_1$, is —$CR_1$=N—$NR_2$— where the C atom is connected to Ar and the terminal N atom is connected directly to $T_1$.

7. An organophotoreceptor according to claim 6 wherein Ar comprises an arylamine group or an aromatic heterocyclic group.

8. An organophotoreceptor according to claim 1 wherein $T_2$ is H, the m value for $X_2$ is 0, $Y_2$ is a bond, $Y_1$, is —$CR_3$=N—N=$CR_4$—, and $T_1$ comprises a thiiranyl group.

9. An organophotoreceptor according to claim 8 wherein Ar comprises an arylamine group or an aromatic heterocyclic group.

10. An organophotoreceptor according to claim 1 wherein $Y_1$ and $Y_2$ are a bond and Ar comprises a bis[(N,N-disubstituted)amino]arylene group.

11. An organophotoreceptor according to claim 10 wherein $T_2$ is H, an alkyl group, an alkenyl group, or an aromatic group.

12. An organophotoreceptor according to claim 1 wherein $Y_1$ and $Y_2$ are a bond, Ar comprises two arylamine groups.

13. An organophotoreceptor according to claim 12 wherein Ar is a bicarbazole group.

14. An organophotoreceptor according to claim 1 wherein Ar comprises an arylamine group, $Y_1$ and $Y_2$ are each independently —$CR_1$=N—$NR_2$—, and $T_1$ and $T_2$, each independently, comprise a thiiranyl group.

15. An organophotoreceptor according to claim 1 wherein the charge transport material is selected from the group consisting of the following formulae:

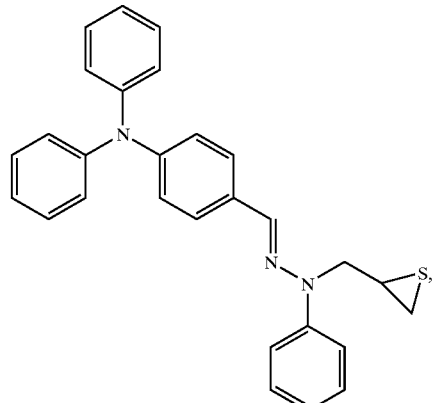

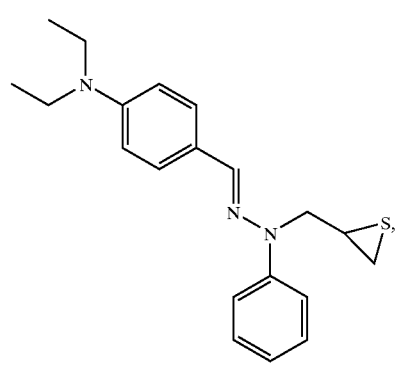

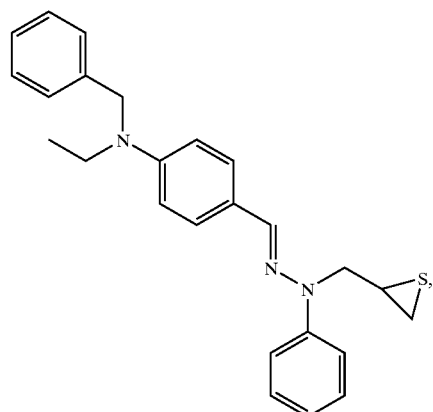

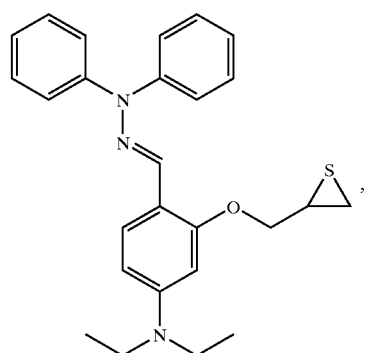

-continued

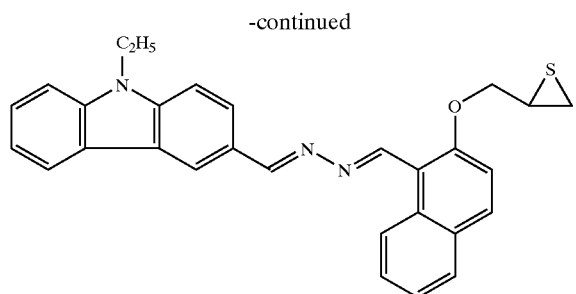,

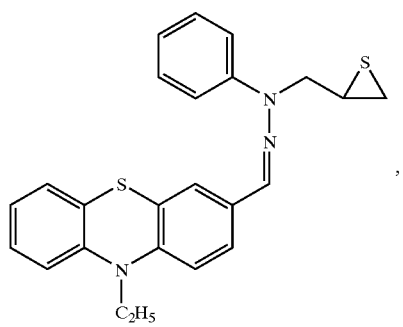,

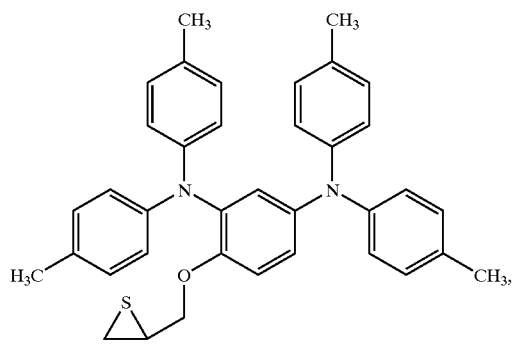,

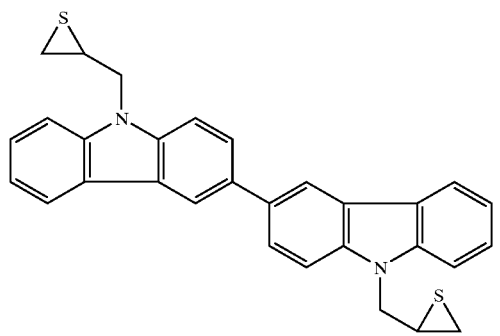,

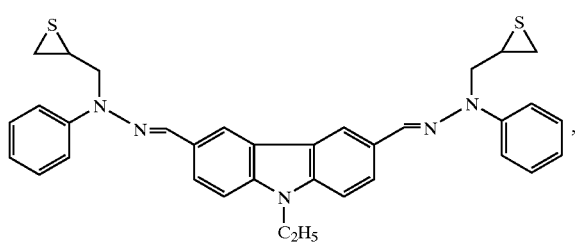,

-continued and

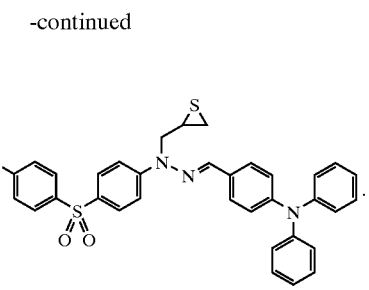.

16. An organophotoreceptor according to claim 1 wherein the photoconductive element further comprises a second charge transport material.

17. An organophotoreceptor according to claim 16 wherein the second charge transport material comprises an electron transport compound.

18. An organophotoreceptor according to claim 1 wherein the photoconductive element further comprises a binder.

19. An electrophotographic imaging apparatus comprising:

(a) a light imaging component; and (b) an organophotoreceptor oriented to receive light from the light imaging component, the organophotoreceptor comprising an electrically conductive substrate and a photoconductive element on the electrically conductive substrate, the photoconductive element comprising:

(i) a charge transport material having the formula

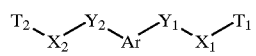

where $Y_1$ and $Y_2$ are, each independently, a bond, —$CR_1$=N—$NR_2$—, or —$CR_3$=N—N=$CR_4$— where $R_1$, $R_2$, $R_3$, and $R_4$ comprise, each independently, H, an alkyl group, an alkenyl group, a heterocyclic group, or an aromatic group;

$X_1$ and $X_2$ are, each independently, a linking group having the formula —$(CH_2)_m$—, branched or linear, where m is an integer between 0 and 20, inclusive, and one or more of the methylene groups is optionally replaced by O, S, C=O, O=S=O, a heterocyclic group, an aromatic group, urethane, urea, an ester group, an $NR_5$ group, a $CHR_6$ group, or a $CR_7R_8$ group where $R_5$, $R_6$, $R_7$, and $R_8$ comprise, each independently, H, hydroxyl group, thiol group, an alkyl group, an alkenyl group, a heterocyclic group, or an aromatic group;

$T_1$ and $T_2$ are, each independently, a thiiranyl group, H, an alkyl group, an alkenyl group, or an aromatic group with the proviso that at least one of $T_1$ and $T_2$ is a thiiranyl group; and Ar comprises an aromatic group with the proviso that when both $Y_1$ and $Y_2$ are a bond and one of $T_1$ and $T_2$ is not a thiiranyl group, Ar comprises a bis[(N,N-disubstituted)amino]aromatic group or a bicarbazole group; and (ii) a charge generating compound.

20. An electrophotographic imaging apparatus according to claim 19 wherein $T_2$ is H, the m value for $X_2$ is 0, $Y_2$ is a bond, $Y_1$ is —$CR_1$=N—$NR_2$— where the C atom is connected to Ar and the terminal N atom is connected to $X_1$, and $T_1$ comprises a thiiranyl group.

21. An electrophotographic imaging apparatus according to claim 20 wherein Ar comprises an arylamine group or an aromatic heterocyclic group.

22. An electrophotographic imaging apparatus according to claim 20 wherein $R_2$ comprises an aromatic group.

23. An electrophotographic imaging apparatus according to claim 22 wherein the aromatic group of $R_2$ has the formula

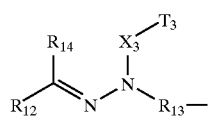

where $R_{12}$ comprises an arylamine group, $R_{13}$ is a linking group comprising an alkyl group, an alkenyl group, or an aryl group, $R_{14}$ comprises H, an alkyl group, an alkenyl group, or an aryl group, $X_3$ has the formula —$(CH_2)_m$—, branched or linear, where m is an integer between 1 and 20, and $T_3$ is a thiiranyl group.

24. An electrophotographic imaging apparatus according to claim 19 wherein the m value for $X_1$ is 0, $T_1$ comprises an aromatic group, $T_2$ comprises a thiiranyl group, $Y_2$ is a bond, and $Y_1$ is —$CR_1$=N—$NR_2$— where the C atom is connected to Ar and the terminal N atom is connected directly to $T_1$.

25. An electrophotographic imaging apparatus according to claim 24 wherein Ar comprises an arylamine group or an aromatic heterocyclic group.

26. An electrophotographic imaging apparatus according to claim 19 wherein $T_2$ is H, the m value for $X_2$ is 0, $Y_2$ is a bond, $Y_1$ is —$CR_3$=N—N=$CR_4$—, and $T_1$ comprises a thiiranyl group.

27. An electrophotographic imaging apparatus according to claim 26 wherein Ar comprises an arylamine group or an aromatic heterocyclic group.

28. An electrophotographic imaging apparatus according to claim 19 wherein $Y_1$ and $Y_2$ are a bond and Ar comprises a bis[(N,N-disubstituted)amino]arylene group.

29. An electrophotographic imaging apparatus according to claim 28 wherein $T_2$ is H, an alkyl group, an alkenyl group, or an aromatic group.

30. An electrophotographic imaging apparatus according to claim 19 wherein $Y_1$ and $Y_2$ are a bond, Ar comprises two arylamine groups.

31. An electrophotographic imaging apparatus according to claim 30 wherein Ar is a bicarbazole group.

32. An electrophotographic imaging apparatus according to claim 19 wherein Ar comprises an arylamine group, $Y_1$ and $Y_2$ are each independently —$CR_1$=N—$NR_2$—, and $T_1$ and $T_2$, each independently, comprise a thiiranyl group.

33. An electrophotographic imaging apparatus according to claim 19 wherein the charge transport material is selected from the group consisting of the following formulae:

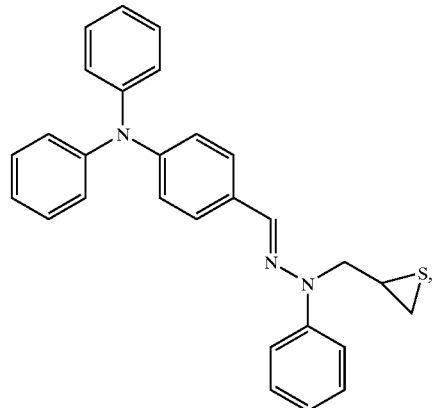

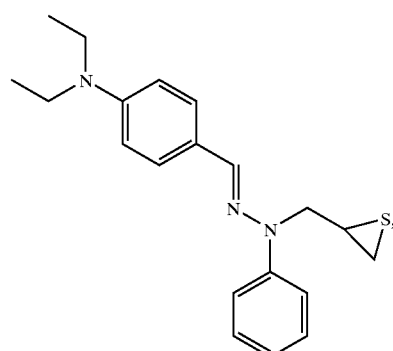

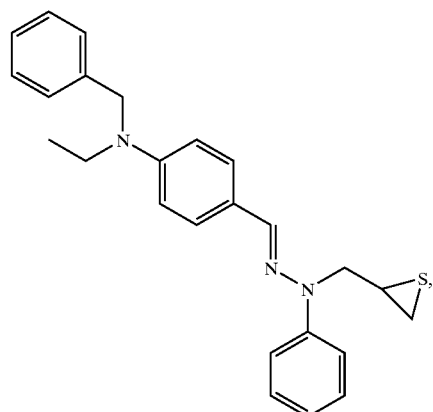

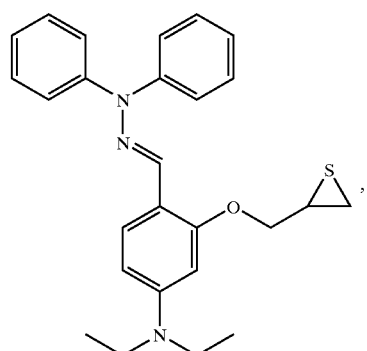

-continued

[chemical structures]

34. An electrophotographic imaging apparatus according to claim 19 wherein the photoconductive element further comprises a second charge transport material.

35. An electrophotographic imaging apparatus according to claim 34 wherein second charge transport material comprises an electron transport compound.

36. An electrophotographic imaging apparatus according to claim 19 further comprising a liquid toner dispenser.

37. An electrophotographic imaging process comprising;
(a) applying an electrical charge to a surface of an organophotoreceptor comprising an electrically conductive substrate and a photoconductive element on the electrically conductive substrate, the photoconductive element comprising
(i) a charge transport material having the formula $$T_2 \diagdown X_2 \diagup Y_2 \diagdown Ar \diagup Y_1 \diagdown X_1 \diagup T_1$$

where $Y_1$ and $Y_2$ are, each independently, a bond, $-CR_1=N-NR_2-$, or $-CR_3=N-N=CR_4-$ where $R_1$, $R_2$, $R_3$, and $R_4$ comprise, each independently, H, an alkyl group, an alkenyl group, a heterocyclic group, or an aromatic group;

$X_1$ and $X_2$ are, each independently, a linking group having the formula $-(CH_2)_m-$, branched or linear, where m is an integer between 0 and 20, inclusive, and one or more of the methylene groups is optionally replaced by O, S, C=O, O=S=O, a heterocyclic group, an aromatic group, urethane, urea, an ester group, an $NR_5$ group, a $CHR_6$ group, or a $CR_7R_8$ group where $R_5$, $R_6$, $R_7$, and $R_8$ comprise, each independently, H, hydroxyl group, thiol group, an alkyl group, an alkenyl group, a heterocyclic group, or an aromatic group;

$T_1$ and $T_2$ are, each independently, a thiiranyl group, H, an alkyl group, an alkenyl group, or an aromatic group with the proviso that at least one of $T_1$ and $T_2$ is a thiiranyl group; and Ar comprises an aromatic group with the proviso that when both $Y_1$ and $Y_2$ are a bond and one of $T_1$ and $T_2$ is not a thiiranyl group, Ar comprises a bis[(N,N-disubstituted)amino]aromatic group or a bicarbazole group; and (ii) a charge generating compound;

(b) imagewise exposing the surface of the organophotoreceptor to radiation to dissipate charge in selected areas and thereby form a pattern of charged and uncharged areas on the surface;

(c) contacting the surface with a toner to create a toned image; and (d) transferring the toned image to substrate.

38. An electrophotographic imaging process according to claim 37 wherein $T_2$ is H, the m value for $X_2$ is 0, $Y_2$ is a bond, $Y_1$, is $-CR_1=N-NR_2-$ where the C atom is connected to Ar and the terminal N atom is connected to $X_1$, and $T_1$ comprises a thiiranyl group.

39. An electrophotographic imaging process according to claim 38 wherein Ar comprises an arylamine group or an aromatic heterocyclic group.

40. An electrophotographic imaging process according to claim 38 wherein $R_2$ comprises an aromatic group.

41. An electrophotographic imaging process according to claim 40 wherein the aromatic group of $R_2$ has the formula

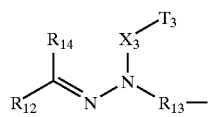

where $R_{12}$ comprises an arylamine group, $R_{13}$ is a linking group comprising an alkyl group, an alkenyl group, or an aryl group, $R_{14}$ comprises H, an alkyl group, an alkenyl group, or an aryl group, $X_3$ has the formula $-(CH_2)_m-$, branched or linear, where m is an integer between 1 and 20, and $T_3$ is a thiiranyl group.

42. An electrophotographic imaging process according to claim 37 wherein the m value for $X_1$ is 0, $T_1$ comprises an aromatic group, $T_2$ comprises a thiiranyl group, $Y_2$ is a bond, and $Y_1$ is $-CR_1=N-NR_2-$ where the C atom is connected to Ar and the terminal N atom is connected directly to $T_1$.

43. An electrophotographic imaging process according to claim 42 wherein Ar comprises an arylamine group or an aromatic heterocyclic group.

44. An electrophotographic imaging process according to claim 37 wherein $T_2$ is H, the m value for $X_2$ is 0, $Y_2$ is a bond, $Y_1$ is $-CR_3=N-N=CR_4-$, and $T_1$ comprises a thiiranyl group.

45. An electrophotographic imaging process according to claim 44 wherein Ar comprises an arylamine group or an aromatic heterocyclic group.

46. An electrophotographic imaging process according to claim 37 wherein $Y_1$ and $Y_2$ are a bond and Ar comprises a bis[(N,N-disubstituted)amino]arylene group.

47. An organophotoreceptor according to claim 46 wherein $T_2$ is H, an alkyl group, an alkenyl group, or an aromatic group.

48. An electrophotographic imaging process according to claim 37 wherein $Y_1$ and $Y_2$ are a bond, Ar comprises two arylamine groups.

49. An electrophotographic imaging process according to claim 48 wherein Ar is a bicarbazole group.

50. An electrophotographic imaging process according to claim 37 wherein Ar comprises an arylamine group, $Y_1$ and $Y_2$ are each independently $-CR_1=N-NR_2-$, and $T_1$ and $T_2$, each independently, comprise a thiiranyl group.

51. An electrophotographic imaging process according to claim 37 wherein the charge transport material is selected from the group consisting of the following formulae:

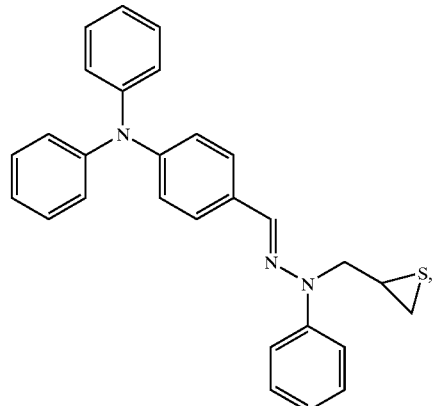

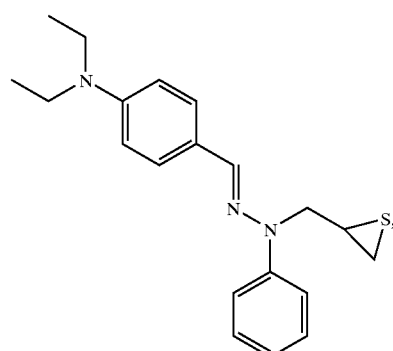

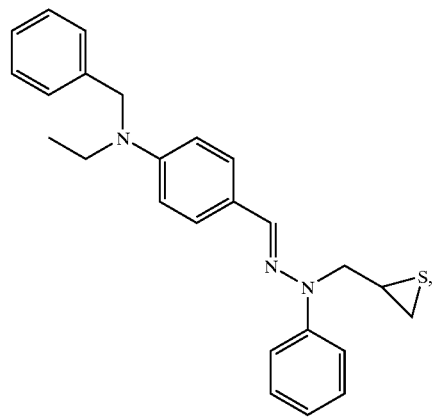

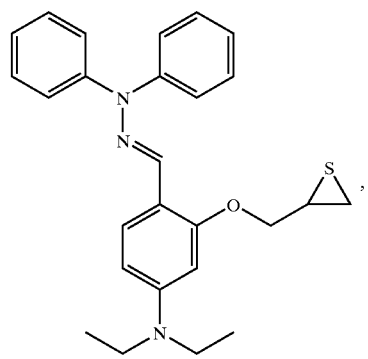

-continued

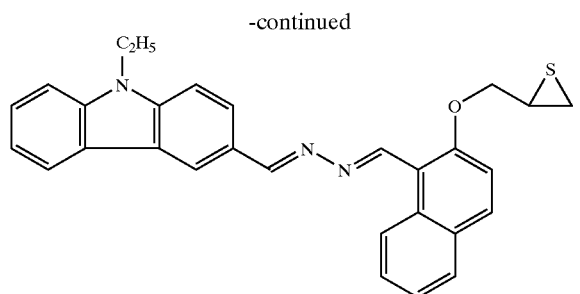,

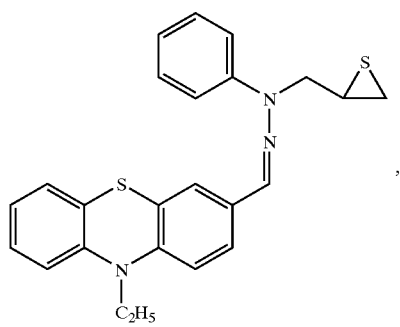,

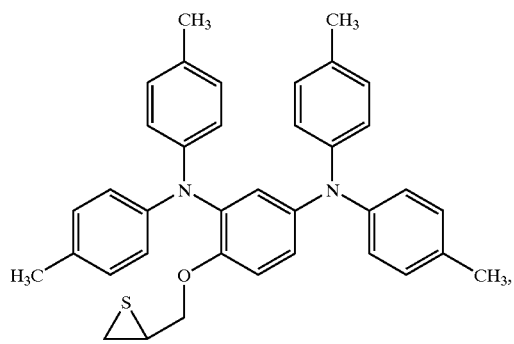,

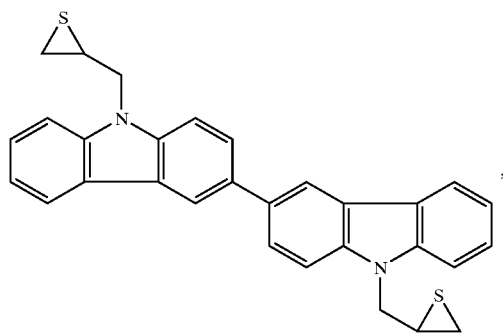,

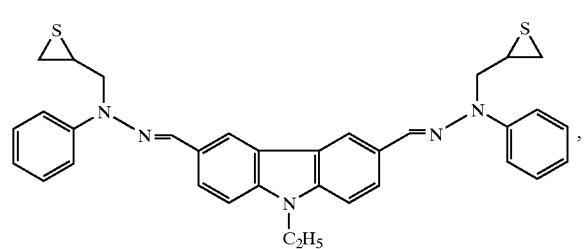,

-continued
and

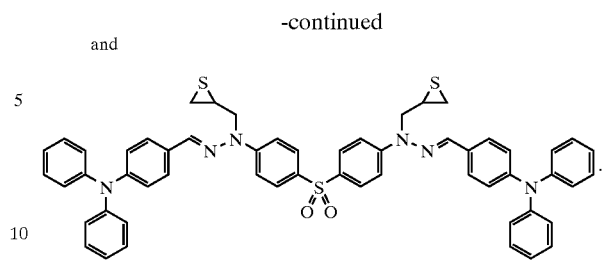.

52. An electrophotographic imaging process according to claim 37 wherein the photoconductive element further comprises a second charge transport material.

53. An electrophotographic imaging process according to claim 52 wherein the second charge transport material comprises an electron transport compound.

54. An electrophotographic imaging process according to claim 37 wherein the photoconductive element further comprises a binder.

55. An electrophotographic imaging process according to claim 37 wherein the toner comprises a liquid toner comprising a dispersion of colorant particles in an organic liquid.

56. A charge transport material having the formula

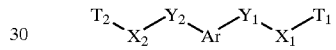

where $Y_1$ and $Y_2$ are, each independently, a bond, $-CR_1=N-NR_2-$, or $-CR_3=N-N=CR_4-$ where $R_1$, $R_2$, $R_3$, and $R_4$ comprise, each independently, H, an alkyl group, an alkenyl group, a heterocyclic group, or an aromatic group;

$X_1$ and $X_2$ are, each independently, a linking group having the formula $-(CH_2)_m-$, branched or linear, where m is an integer between 0 and 20, inclusive, and one or more of the methylene groups is optionally replaced by O, S, C=O, O=S=O, a heterocyclic group, an aromatic group, urethane, urea, an ester group, an $NR_5$ group, a $CHR_6$ group, or a $CR_7R_8$ group where $R_5$, $R_6$, $R_7$, and $R_8$ comprise, each independently, H, hydroxyl group, thiol group, an alkyl group, an alkenyl group, a heterocyclic group, or an aromatic group;

$T_1$ and $T_2$ are, each independently, a thiiranyl group, H, an alkyl group, an alkenyl group, or an aromatic group with the proviso that at least one of $T_1$ and $T_2$ is a thiiranyl group; and Ar comprises an aromatic group with the proviso that when both $Y_1$ and $Y_2$ are a bond and one of $T_1$ and $T_2$ is not a thiiranyl group, Ar comprises a bis[(N,N-disubstituted)amino]aromatic group or a bicarbazole group.

57. A charge transport material according to claim 56 wherein $T_2$ is H, the m value for $X_2$ is 0, $Y_2$ is a bond, $Y_1$, is $-CR_1=N-NR_2-$ where the C atom is connected to Ar and the terminal N atom is connected to $X_1$, and $T_1$ comprises a thiiranyl group.

58. A charge transport material according to claim 57 wherein Ar comprises an arylamine group or an aromatic heterocyclic group.

59. A charge transport material according to claim 57 wherein $R_2$ comprises an aromatic group.

60. A charge transport material according to claim 59 wherein the aromatic group of $R_2$ has the formula

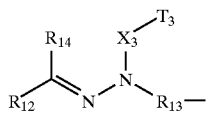

where $R_{12}$ comprises an arylamine group, $R_{13}$ is a linking group comprising an alkyl group, an alkenyl group, or an aryl group, $R_{14}$ comprises H, an alkyl group, an alkenyl group, or an aryl group, $X_3$ has the formula —$(CH_2)_m$—, branched or linear, where m is an integer between 1 and 20, and $T_3$ is a thiiranyl group.

61. A charge transport material according to claim 56 wherein the m value for $X_1$ is 0, $T_1$ comprises an aromatic group, $T_2$ comprises a thiiranyl group, $Y_2$ is a bond, and $Y_1$ is —$CR_1$=N—$NR_2$— where the C atom is connected to Ar and the terminal N atom is connected directly to $T_1$.

62. A charge transport material according to claim 61 wherein Ar comprises an arylamine group or an aromatic heterocyclic group.

63. A charge transport material according to claim 56 wherein $T_2$ is H, the m value for $X_2$ is 0, $Y_2$ is a bond, $Y_1$ is —$CR_3$=N—N=$CR_4$—, and $T_1$ comprises a thiiranyl group.

64. A charge transport material according to claim 63 wherein Ar comprises an arylamine group or an aromatic heterocyclic group.

65. A charge transport material according to claim 56 wherein $Y_1$ and $Y_2$ are a bond and Ar comprises a bis[(N, N-disubstituted)amino]arylene group.

66. A charge transport material according to claim 65 wherein $T_2$ is H, an alkyl group, an alkenyl group, or an aromatic group.

67. A charge transport material according to claim 56 wherein $Y_1$ and $Y_2$ are a bond, Ar comprises two arylamine groups.

68. A charge transport material according to claim 67 wherein Ar is a bicarbazole group.

69. A charge transport material according to claim 56 wherein Ar comprises an arylamine group, $Y_1$ and $Y_2$ are each independently —$CR_1$=N—$NR_2$—, and $T_1$ and $T_2$, each independently, comprise a thiiranyl group.

70. A charge transport material according to claim 56 wherein the charge transport material is selected from the group consisting of the following formulae:

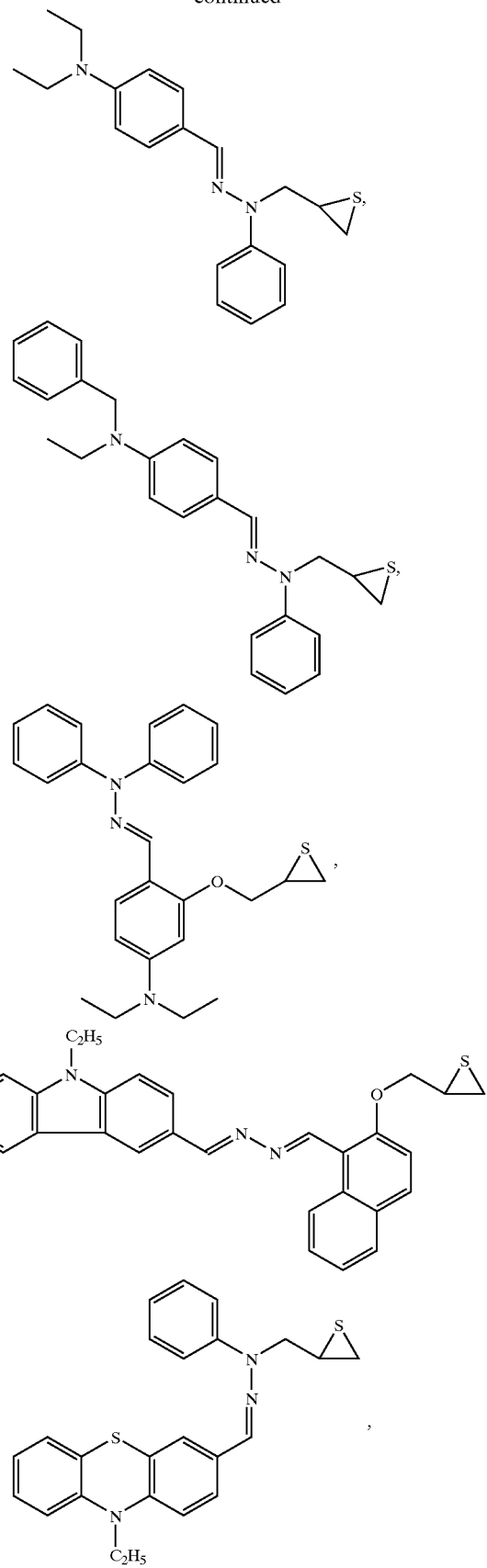

-continued

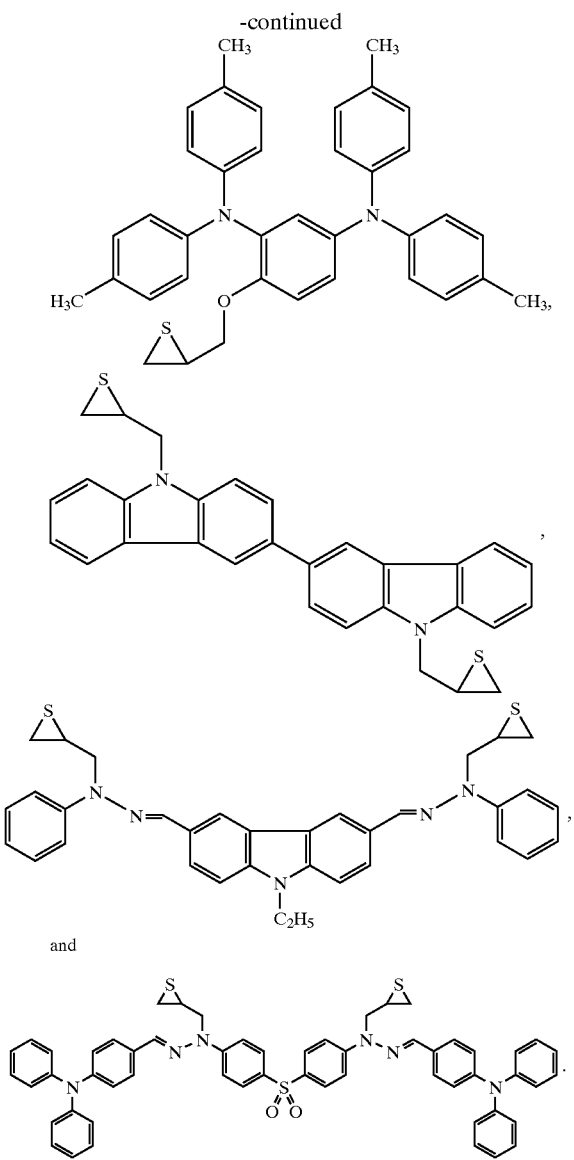

and

71. A polymeric charge transport material prepared by the reaction of a functional group in a polymeric binder with at least a thiiranyl group in a compound having the formula

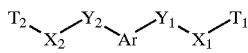

where $Y_1$ and $Y_2$ are, each independently, a bond, —$CR_1$=N—$NR_2$—, or —$CR_3$=N—N=$CR_4$— where $R_1$, $R_2$, $R_3$, and $R_4$ comprise, each independently, H, an alkyl group, an alkenyl group, a heterocyclic group, or an aromatic group;

$X_1$ and $X_2$ are, each independently, a linking group having the formula —$(CH_2)_m$—, branched or linear, where m is an integer between 0 and 20, inclusive, and one or more of the methylene groups is optionally replaced by O, S, C=O, O=S=O, a heterocyclic group, an aromatic group, urethane, urea, an ester group, an $NR_5$ group, a $CHR_6$ group, or a $CR_7R_8$ group where $R_5$, $R_6$, $R_7$, and $R_8$ comprise, each independently, H, hydroxyl group, thiol group, an alkyl group, an alkenyl group, a heterocyclic group, or an aromatic group;

$T_1$ and $T_2$ are, each independently, a thiiranyl group, H, an alkyl group, an alkenyl group, or an aromatic group with the proviso that at least one of $T_1$ and $T_2$ is a thiiranyl group; and Ar comprises an aromatic group with the proviso that when both $Y_1$, and $Y_2$ are a bond and one of $T_1$ and $T_2$ is not a thiiranyl group, Ar comprises a bis[(N,N-disubstituted)amino]aromatic group or a bicarbazole group.

72. A polymeric charge transport material according to claim 71 wherein the functional group of the binder is selected from the group consisting of hydroxyl group, carboxyl group, an amino group, and thiol group.

73. A polymeric charge transport material according to claim 71 wherein a crosslinking agent is bonded between the thiiranyl group and the functional group of the binder.

74. An organophotoreceptor comprising an electrically conductive substrate and a photoconductive element on the electrically conductive substrate, the photoconductive element comprising:

(a) a polymeric charge transport compound prepared by the reaction of a functional group in a polymeric binder with at least a thiiranyl group in a compound having the formula

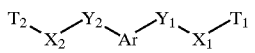

where $Y_1$ and $Y_2$ are, each independently, a bond, —$CR_1$=N—$NR_2$—, or —$CR_3$=N—N=$CR_4$— where $R_1$, $R_2$, $R_3$, and $R_4$ comprise, each independently, H, an alkyl group, an alkenyl group, a heterocyclic group, or an aromatic group;

$X_1$ and $X_2$ are, each independently, a linking group having the formula —$(CH_2)_m$—, branched or linear, where m is an integer between 0 and 20, inclusive, and one or more of the methylene groups is optionally replaced by O, S, C=O, O=S=O, a heterocyclic group, an aromatic group, urethane, urea, an ester group, an $NR_5$ group, a $CHR_6$ group, or a $CR_7R_8$ group where $R_5$, $R_6$, $R_7$, and $R_8$ comprise, each independently, H, hydroxyl group, thiol group, an alkyl group, an alkenyl group, a heterocyclic group, or an aromatic group;

$T_1$ and $T_2$ are, each independently, a thiiranyl group, H, an alkyl group, an alkenyl group, or an aromatic group with the proviso that at least one of $T_1$ and $T_2$ is a thiiranyl group; and Ar comprises an aromatic group with the proviso that when both $Y_1$ and $Y_2$ are a bond and one of $T_1$ and $T_2$ is not a thiiranyl group, Ar comprises a bis[(N,N-disubstituted)amino]arylene group or a bicarbazole group; and (b) a charge generating compound.

75. An organophotoreceptor according to claim 74 wherein the photoconductive element further comprises an electron transport compound.

76. An organophotoreceptor according to claim 74 wherein the functional group of the binder is selected from the group consisting of hydroxyl group, carboxyl group, an amino group, and thiol group.

* * * * *